United States Patent [19]

Barth

[11] 4,066,657

[45] Jan. 3, 1978

[54] 2-[(CARBOXY)(TRIPHENYLME-THYLAMINO)METHYL]-5,5-DIMETHYL-3-THIAZOLINE

[75] Inventor: Wayne E. Barth, East Lyme, Conn.

[73] Assignee: Pfizer Inc., New York, N.Y.

[21] Appl. No.: 736,956

[22] Filed: Oct. 29, 1976

Related U.S. Application Data

[60] Division of Ser. No. 680,423, April 26, 1976, Pat. No. 4,031,077, which is a continuation-in-part of Ser. No. 619,634, Oct. 6, 1975, abandoned.

[51] Int. Cl.² .......................................... C07D 277/10
[52] U.S. Cl. ........................................... 260/306.7 R
[58] Field of Search ............................... 260/306.7 R

[56] References Cited

U.S. PATENT DOCUMENTS 3,816,445  6/1974  Dubs et al. .................... 260/306.7 R 3,931,208  1/1976  Offermanns et al. ......... 260/306.7 R

*Primary Examiner*—Richard J. Gallagher
*Attorney, Agent, or Firm*—Connolly And Hutz

[57] ABSTRACT

The present invention discloses novel 6-acylamino-2,2-dimethyl-3-phosphonopenams and certain lower alkyl esters thereof possessing antibacterial activity, methods for their production, and intermediates therefor; the production comprises the steps of reacting 6-triphenyl-methylamino-2,2-dimethylpenam-3-carboxylic acid with lead tetraacetate to form the corresponding 3-acetoxy compound, the latter is converted to α-triphenylmethylamino-5,5-dimethyl-3-thiazoline-2-acetic acid which is condensed with dimethyl phosphite to produce α-triphenylmethylamino-5,5-dimethyl-4(0,0-dimethylphosphono)-thiazolidine-2-acetic acid which is cyclized to 6-triphenylmethylamino-2,2-dimethyl-3-(0,0-dimethylphosphono)penam and the latter is subsequently deblocked and acylated.

1 Claim, No Drawings

2-[(CARBOXY)(TRIPHENYLMETHYLAMINO)ME-THYL]-5,5-DIMETHYL-3-THIAZOLINE

CROSS-REFERENCE TO RELATED APPLICATION

This is a division of application Ser. No. 680,423 filed Apr. 26, 1976, now U.S. Pat. No. 4,031,077, which in turn is a continuation-in-part of my copending application Ser. No. 619,634, filed Oct. 6, 1975 and now abandoned.

BACKGROUND OF THE INVENTION

1. Field of the Invention

This invention relates to novel antibacterial agents which are of value as animal feed supplements, and to novel intermediates for their production. More specifically, the antibacterial compounds of the invention are certain 6-acylamino-2,2-dimethyl-3-phosphonopenams, the corresponding 6-acylamino-2,2-dimethyl-3-(O-methylphosphono)penams and 6-acylamino-2,2-dimethyl-3-(O,O-dimethylphosphono)penams and pharmaceutically acceptable salts thereof, as well as processes and novel intermediates for their production.

2. Description of the Prior Art

In spite of the large number of penam derivatives which have been proposed for use as antibacterial agents, there still exists a need for new agents.

The vast majority of penam compounds disclosed in the prior art have carboxylic acid group (or a salt thereof) attached to the 3-position. However, penam compounds with other carboxylic acid derivatives at the C-3 locus are also known. Penam-3-carboxylic acid esters have been disclosed, for example, by Kirchner et al., *Journal of Organic Chemistry*, 14, 388 (1949); Carpenter, *Journal of the American Chemical Society*, 70, 2964 (1948); Johnson, *Journal of the American Chemical Society*, 75, 3636 (1953); Barnden et al., *Journal of the Chemical Society* (London), 3733 (1953) and Jansen and Russell, *Journal of the Chemical Society* (London), 2127 (1965); and penam-3-carboxamides have been reported, for example, by Holysz and Stavely, *Journal of the American Chemical Society*, 72, 4760 (1950) and Huang et al., *Antimicrobial Agents and Chemotherapy*, 493 (1963). Peron et al. (*Journal of Medicinal Chemistry*, 7, 483 [1964])prepared several 6-(substituted amino)-2,2-dimethyl-penam-3-carboxylic acid azides, which were subsequently converted into the corresponding 3-isocyanates and 3-benzylcarbamates. Peron et al. (loc. cit.) also reported certain 3-(hydroxymethyl)penam derivatives. Dehydration of the simple amide of benzylpenicillin yields the corresponding nitrile (Khokhlov et al., *Doklady Akad, Sci. Nauk S.S.S.R.*, 135, 875 [1960]).

3-(5-Tetrazolyl)penams were disclosed in Belgian Pat. No. 821,163.

Phosphorylated penicillanic and cephalosporanic acids, prepared by reaction of the corresponding 3- or 4-carboxylic acids, respectively, with a phosphorus halide are reported in U.S. Pat. No. 3,875,152. α-(phosphono)- and α-(phosphonoalkyl)-cephalosporins in which the phosphorus containing group is incorporated into the 7-acyl side chain are the subject of U.S. Pat. No. 3,870,713.

West German Specification No. 2,364,735 disclosed cephalosporins in which phosphono, sulfo or sulfonamido groups are attached at the 4-position of the cephem nucleus by total synthesis.

Regarding the prior art pertinent to the disclosed intermediates for preparation of the compounds of the invention, Heusler, *Helvetica Chimica Acta*, 55, 388 (1972), has reported the synthesis of α-phenoxyacetamido-5,5-dimethyl-3-thiazoline-2-acetic acid piperidide by reacting 6-phenoxyacetamido-2,2-dimethyl-3-hydroxypenam with piperidine benzoate in acetontrile as solvent. Heusler (loc. cit.), and Barton et al., *J. Chem. Soc., Perkin I*, 599 (1973), have reported on methods of synthesis of 3-hydroxy-penam derivatives containing 6-phenylacetamido and 6-phenoxyacetamido moieties. Barton (loc. cit. and references therein) has also reported the corresponding S-oxides. However, 6-triphenylmethylamino-2,2-dimethyl-3-acetoxypenam is not previously disclosed and neither is the lead tetraacetate method for preparation of 3-acetoxypenams.

For the sake of convenience, the compounds described herein are identified as derivatives of penam. The term "penam" has been defined in the *J. Am. Chem. Soc.*, 75, 3293 (1953), as referring to the structure:

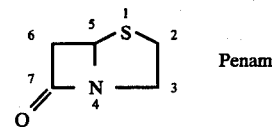

Penam

Using this terminology, the well-known antibiotic penicillin G is designated as 6-(2-phenylacetamido)-2,2-dimethylpenam-3-carboxylic acid. The hydrogen methyl phosphonate analog of penicillin G, formula (Ib) below, wherein $R^1$ is phenyl and Q is hydrogen, is designated as 6-(2-phenylacetamido)-2,2-dimethyl-3-(O-methylphosphono)penam. The corresponding dimethyl phosphonate is designated as 6-(2-phenylacetamido)-2,2-dimethyl-3-(O,O-dimethylphosphono)penam and the corresponding dibasic phosphonic acid is designated as 6-(2-phenylacetamido)-2,2-dimethyl-3-phosphonopenam.

SUMMARY OF THE INVENTION

It is an object of the present invention to provide novel penam-3-phosphonates which are valuable new antibacterial agents useful as animal feed supplements. The said novel penams are those of the formula (I)

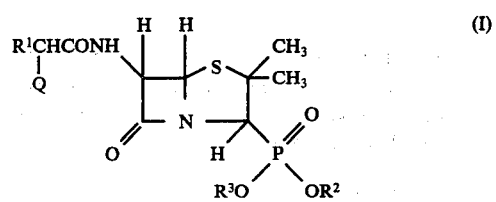

and the pharmaceutically acceptable salts thereof wherein $R^2$ and $R^3$ are the same or different and are selected from the group consisting of hydrogen and methyl;

$R^1$ is selected from the group consisting of phenyl, phenoxy, 1,4-cyclohexadienyl, thienyl and phenyl monosubstituted by a member selected from the group consisting of hydroxy, and aminomethyl, and Q is selected from the group consisting of hydrogen, amino, carboxy and sulfo; provided that:

when $R^1$ is selected from the group consisting of phenoxy and phenyl monosubstituted by aminomethyl, Q is hydrogen;

when Q is carboxy, $R^1$ is selected from the group consisting of phenyl and thienyl;

and when Q is sulfo, $R^1$ is phenyl.

It is a further object of this invention to provide novel intermediates for the production of said compounds of formula (I). These novel intermediates are 6-triphenylmethylamino-2,2-dimethyl-3-acetoxypenam, 6-triphenylmethylamino-2,2-dimethyl-3-hydroxypenam, a compound of the formula

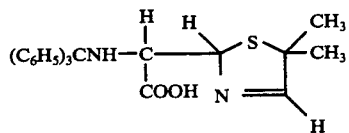
(II)

and the salts thereof; a compound of the formula (III)

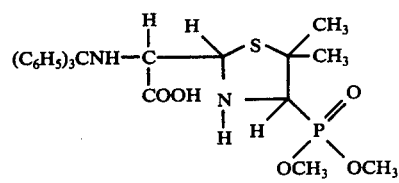
(III)

and the salts thereof; a compound of the formula (IX)

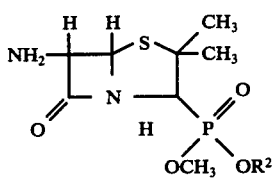
(IX)

and salts thereof; wherein $R^2$ is hydrogen or methyl; and a compound of the formula (X)

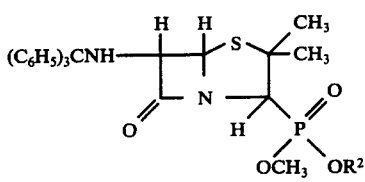
(X)

and the salts thereof; wherein $R^2$ is hydrogen or methyl.

Also provided are processes for the production of said intermediates and processes for the production of a compound of the formula (Ib)

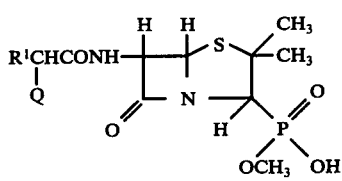
(Ib)

a salt or functional derivative thereof;

wherein $R^1$ is selected from the group consisting of phenyl, phenoxy, 1,4-cyclohexadienyl, thienyl and phenyl monosubstituted by a member selected from the group consisting of hydroxy and aminomethyl, and Q is selected from the group consisting of hydrogen, amino, carboxy and sulfo; provided that:

when $R^1$ is selected from the group consisting of phenoxy and phenyl monosubstituted by aminomethyl, Q is hydrogen;

when Q is carboxy, $R^1$ is selected from the group consisting of phenyl and thienyl;

and when Q is sulfo, $R^1$ is phenyl;

which comprises the steps of:

a. reacting a compound of the formula (IX)

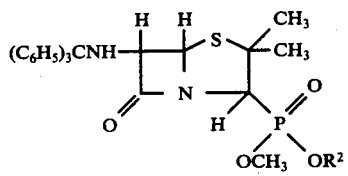
(IX)

wherein $R^2$ is hydrogen or methyl; under suitable acidic conditions to remove the triphenylmethyl amino protectecting group to afford a compound of the formula (X)

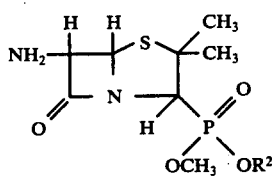
(X)

or a salt thereof;

wherein $R^2$ is as defined above;

b. reacting said compound of formula (X) with a suitable organic acylating agent which introduces the radical

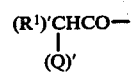

at the 6-amino group to obtain a compound of the formula (XI)

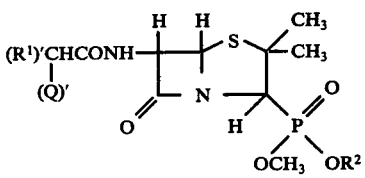
(XI)

or a salt thereof;

wherein $R^2$ is as defined above, $(R^1)'$ is $R^1$ as defined above or is phenyl monosubstituted by a member selected from the group consisting of protected aminomethyl, and azidomethyl, and $(Q)'$ is Q as defined above or is a member of the group consisting of protected amino and azido; provided that when $(R^1)'$ is phenoxy or phenyl monosubstituted by a member selected from the group consisting of aminomethyl, protected aminomethyl and azidomethyl, $(Q)'$ is hydrogen;

c. reacting said compound of formula (XI) containing said protected amino, protected aminomethyl and azido to obtain said compound of formula (Ib) or (Ia).

[Structure (Ia): R¹CHCONH-Q / β-lactam-thiazolidine with P(=O)(OCH₃)(OCH₃)]

d. further reacting said compound of forumula (Ia) to obtain said compound of formula (Ib).

The invention also provides processes for production of a compound of the formula (XVI)

[Structure (XVI): R⁵NH- / β-lactam-thiazolidine with P(=O)(OCH₃)(OH)]

and salts thereof, wherein $R^5$ is a member selected from the group consisting of hydrogen and triphenylmethyl which comprises the step of reacting a compound of the formula (XV)

[Structure (XV): R⁵NH- / β-lactam-thiazolidine with P(=O)(OCH₃)(OCH₃)]

under suitable conditions. It is preferred that this process be carried out by reacting said compound (XV) with lithium iodide in the presence of an organic solvent.

Further, the invention provides a process for preparing a compound of the formula (Ic)

[Structure (Ic): R¹CHCONH-Q / β-lactam-thiazolidine with P(=O)(OH)(OH)]

wherein $R^1$ and Q are as previously defined, which comprises the steps of:

a. reacting a compound of the formula (XII)

[Structure (XII): R¹CHCONH-Q / β-lactam-thiazolidine with P(=O)(OCH₃)(OR²)]

wherein $R^2$ is hydrogen or methyl; with lithium iodide and a silylating agent in the presence of a molar excess of a tertiary amine, b. treatment with water.

DETAILED DESCRIPTION OF THE INVENTION

The novel compounds disclosed in the present invention are those of the formula

[Structure: R¹CHCONH-Q / β-lactam-thiazolidine with P(=O)(OR₃)(OR₂)]

and the salts thereof;
wherein $R^2$ and $R^3$ are the same or different and are hydrogen or alkyl having from one to four carbon atoms;

$R^1$ is selected from the group consisting of phenyl, phenoxy, 1,4-cyclohexadienyl, thienyl and phenyl monosubstituted by a member selected from the group consisting of hydroxy and aminomethyl, and Q is selected from the group consisting of hydrogen, amino, carboxy and sulfo; provided that:

when $R^1$ is selected from the group consisting of phenoxy and phenyl monosubstituted by aminomethyl, Q is hydrogen;

when Q is carboxy, $R^1$ is selected from the group consisting of phenyl and thienyl;

and when Q is sulfo, $R^1$ is phenyl.

Preferred novel and valuable compounds of the invention are those of formula (I)

[Structure (I): R¹CHCONH-Q / β-lactam-thiazolidine with P(=O)(OR³)(OR²)]

and the pharmaceutically acceptable salts thereof;
wherein $R^2$ and $R^3$ are the same or different and are selected from the group consisting of hydrogen and methyl; $R^1$ is selected from the group consisting of phenyl, phenoxy, 1,4-cyclohexadienyl, thienyl and phenyl monosubstituted by a member selected from the group consisting of hydroxy and aminomethyl, and Q is selected from the group consisting of hydrogen, amino, carboxy and sulfo; provided that:

when $R^1$ is selected from the group consisting of phenoxy and phenyl monosubstituted by aminomethyl, Q is hydrogen;

when Q is carboxy, $R^1$ is selected from the group consisting of phenyl and thienyl;

and when Q is sulfo, $R^1$ is phenyl.

Compounds of formula (I) wherein $R^2$ and $R^3$ are methyl are also herein referred to as compounds of formula (Ia). Compounds of formula (I) wherein $R^2$ is H and $R^3$ is methyl are herein referred to as compounds of formula (Ib); and those of formula (I) in which $R^2$ and $R^3$ are hydrogen are referred to as compounds of formula (Ic).

The compounds of formula (Ia) are of value both as intermediates for industrial production of the above compounds of formulae (Ib) and (Ic), as well as being capable of serving as precursors of the monobasic phosphonates of formula (Ib) and the corresponding dibasic phosphonates (Ic) in suitable biological systems which cause hydrolysis of said phosphonate ester groups. Suitable biological systems are those which possess enzymes capable of hydrolyzing phosphorus-containing ester groups, such as those enzymes present in many bacteria and animals including humans.

When the compounds of formula (Ia) are employed as said intermediates for industrial production of compounds of formulae (Ib) and (Ic), salts of compounds of formula (Ia) other than those which are pharmaceutically acceptable as well as solvates such as the hydrates of compounds of formula (Ia) are useful for example in purifying and isolating said compounds of formulae (Ia), (Ib) and (Ic).

Examples of valuable compounds of the invention are:

6-(2-phenylacetamido)-2,2-dimethyl-3-phosphonopenam,
6-(2-phenylacetamido)-2,2-dimethyl-3-(O-methylphosphono)penam,
6-(2-phenylacetamido)-2,2-dimethyl-3-(O,O-dimethylphosphono)penam,
6-(2-phenoxyacetamido)-2,2-dimethyl-3-phosphonopenam,
6-(2-phenoxyacetamido)-2,2-dimethyl-3-(O-methylphosphono)penam,
6-(2-phenoxyacetamido)-2,2-dimethyl-3-(O,O-dimethylphosphono)penam,
6-(L-2-amino-2-phenylacetamido)-2,2-dimethyl-3-phosphonopenam,
6-(DL-2-amino-2-phenylacetamido)-2,2-dimethyl-3-(O-methylphosphono)penam,
6-(D-2-amino-2-phenylacetamido)-2,2-dimethyl-3-(O,O-dimethylphosphono)penam,
6-(DL-2-amino-2-[1,4-cyclohexadienyl]acetamido)-2,2-dimethyl-3-phosphonopenam,
6-(D-2-amino-2-[1,4-cyclohexadienyl]acetamido)-2,2-dimethyl-3-(O,O-dimethylphosphono)penam,
6-(D-2-amino-2-[3-thienyl]acetamido)-2,2-dimethyl-3-phosphonopenam,
6-(DL-2-amino-2-[3-thienyl]acetamido)-2,2-dimethyl-3-(O-methylphosphono)penam,
6-(2-[2-aminomethylphenyl]acetamido)-2,2-dimethyl-3-phosphonopenam,
6-(2-[2-aminomethylphenyl]acetamido)-2,2-dimethyl-3-(O,O-dimethylphosphono)penam,
6-(2-thienyl]acetamido)-2,2-dimethyl-3-phosphonopenam,
6-(2-[2-thienyl]acetamido-2,2-dimethyl-3-(O-methylphosphono)penam,
6-(2-[3-thienyl]acetamido)-2,2-dimethyl-3-(O,O-dimethylphosphono)penam,
6-(2-carboxy-2-phenylacetamido)-2,2-dimethyl-3-phosphonopenam,
6-(2-carboxy-2-phenylacetamido)-2,2-dimethyl-3-(O-methylphosphono)penam
6-(2-carboxy-2-phenylacetamido)-2,2-dimethyl-3-(O,O-dimethylphosphono)penam,
6-(2-carboxy-2-[2-thienyl]acetamido)-2,2-dimethyl-3-phosphonopenam,
6-(2-carboxy-2-[2-thienyl]acetamido)-2,2-dimethyl-3-(O,O-dimethylphosphono)penam,
6-(2-carboxy-2-[3-thienyl]acetamido)-2,2-dimethyl-3-(O-methylphosphono)penam,
6-(D-2-sulfo-2-phenylacetamido)-2,2-dimethyl-3-phosphonopenam,
6-(D-2-sulfo-2-phenylacetamido)-2,2-dimethyl-3-(O-methylphosphono)penam,
6-(DL-2-sulfo-2-phenylacetamido)-2,2-dimethyl-3-(O,O-dimethylphosphono)penam.

Compounds of the invention which are extremely valuable are:
6-(2-phenylacetamido)-2,2-dimethyl-3-phosphonopenam,
6-(2-phenylacetamido)-2,2-dimethyl-3-(O-methylphosphono)penam,
6-(2-phenoxyacetamido)-2,2-dimethyl-3-phosphonopenam,
6-(2-phenoxyacetamido)-2,2-dimethyl-3-(O-methylphosphono)penam,
6-(D-2-amino-2-phenylacetamido)-2,2-dimethyl-3-phosphonopenam,
6-(D-2-amino-2-phenylacetamido)-2,2-dimethyl-3-(O-methylphosphono)penam,
6-(D-2-amino-2-[p-hydroxyphenyl]acetamido)-2,2-dimethyl-3-phosphonopenam,
6-(D-2-amino-2-[p-hydroxyphenyl]acetamido)-2,2-dimethyl-3-(O-methylphosphono)penam,
6-(DL-2-amino-2-[p-hydroxyphenyl]acetamido)-2,2-dimethyl-3-phosphonopenam,
6-(DL-2-amino-2-[p-hydroxyphenyl]acetamido)-2,2-dimethyl-3-(O-methylphosphono)penam,
6-(D-2-amino-2-[1,4-cyclohexadienyl]acetamido)-2,2-dimethyl-3-phosphonopenam,
6-(D-2-amino-2-[1,4-cyclohexadienyl]acetamido)-2,2-dimethyl-3-(O-methylphosphono)penam,
6-(DL-2-amino-2-[3-thienyl]acetamido)-2,2-dimethyl-3-phosphonopenam,
6-(DL-2-amino-2-[3-thienyl]acetamido)-2,2-dimethyl-3-(O-methylphosphono)penam,
6-(D-2-amino-2-[3-thienyl]acetamido)-2,2-dimethyl-3-(O-methylphosphono)penam,
6-(2-[2-aminomethylphenyl]acetamido)-2,2-dimethyl-3-phosphonopenam,
6-(2-[2-aminomethylphenyl]acetamido)-2,2-dimethyl-3-(O-methylphosphono)penam,
6-(2-[2-thienyl]acetamido)-2,2-dimethyl-3-phosphonopenam,
6-(2-[2-thienyl]acetamido)-2,2dimethyl-3-(O-methylphosphono)penam,
6-(2-[3-thienyl]acetamido)-2,2-dimethyl-3-phosphonopenam,
6-(2-[3-thienyl]acetamido)-2,2-dimethyl-3-(O-methylphosphono)penam,
6-(2-carboxy-2-phenylacetamido)-2,2-dimethyl-3-phosphonopenam,
6-(2-carboxy-2-phenylacetamido)-2,2-dimethyl-3-(O-methylphosphono)penam
6-(2-carboxy-2-[2-thienyl]acetamido)-2,2-dimethyl-3-phosphonopenam,
6-(2-carboxy-2-[2-thienyl]acetamido)-2,2-dimethyl-3-(O-methylphosphono)penam,
6-(2-carboxy-2-[3-thienyl]acetamido)-2,2-dimethyl-3-phosphonopenam,
6-(2-carboxy-2-[3-thienyl]acetamido)-2,2-dimethyl-3-(O-methylphosphono)penam,
6-(D-2-sulfo-2-phenylacetamido)-2,2-dimethyl-3-phosphonopenam,
6-(D-2-sulfo-2-phenylacetamido)-2,2-dimethyl-3-(O-methylphosphono)penam.

As will be recognized by one skilled in the art, the acyl group $$R^1CHCO-$$
$$|$$
$$Q$$

can contain an asymmetric center which can exist in one of two forms, the so-called D- and L- forms. Both forms of the asymmetric center, and all combinations of each of the forms, are to be considered within the scope and purview of this invention.

The novel compounds of the inventions are prepared employing the well-known 6-aminopenicillanic acid (6-APA) as starting material. The following flow sheets illustrate some of the processes by which the preferred compounds of the invention can be prepared. In Flow Sheet I the sequence of reactions to form the compounds represented by the formulae (IX), (X), (XI) and (XII) are outlined in a general manner. The reaction sequences leading to compounds of formulae (Ia), (Ib) and (Ic), starting with compound (III) are depicted in Flow Sheet II.

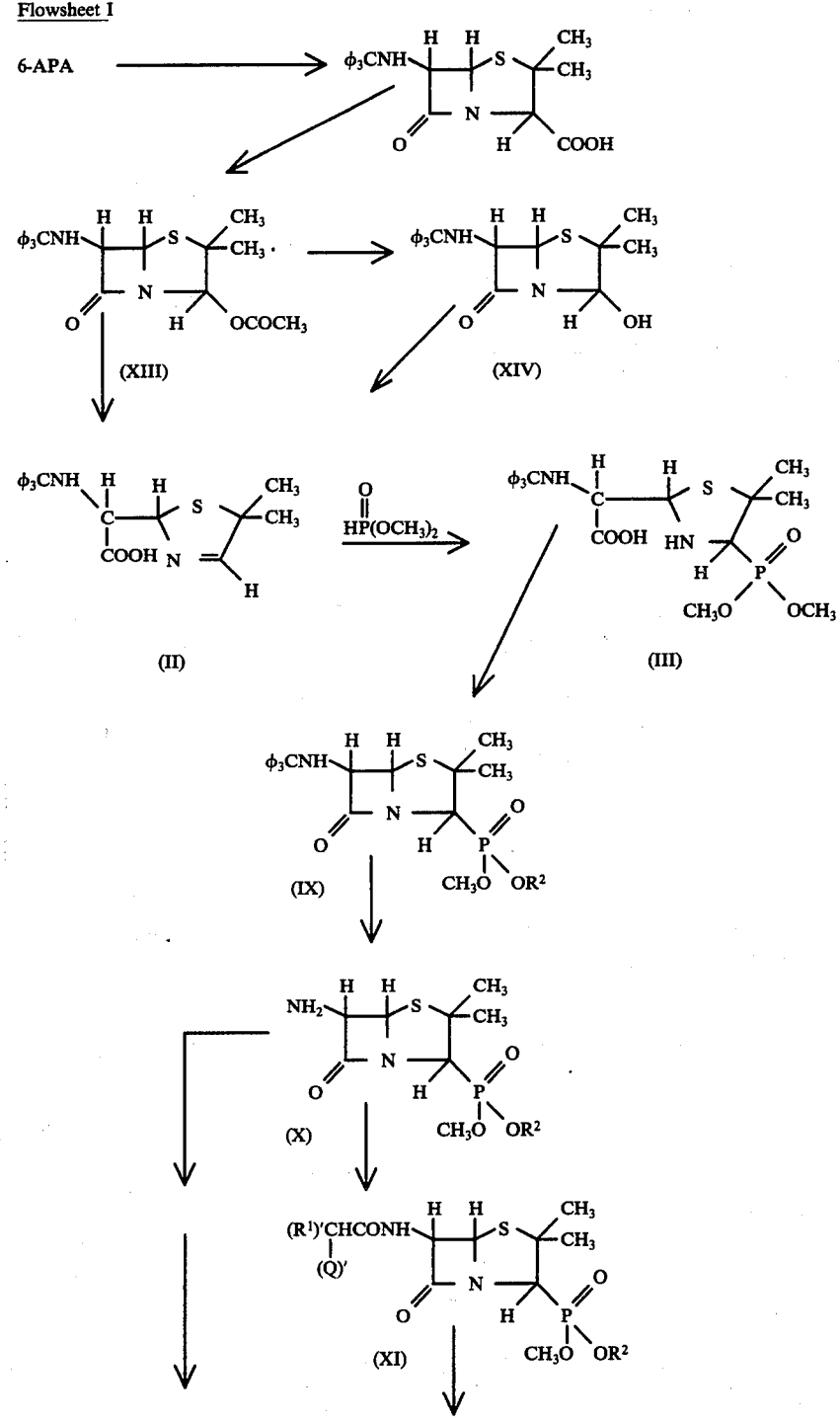

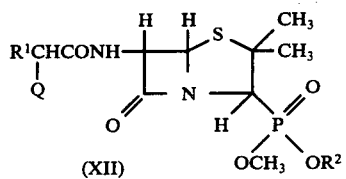
(XII)
Note:
φ = C₆H₅—
R² is hydrogen or methyl
Flowsheet II
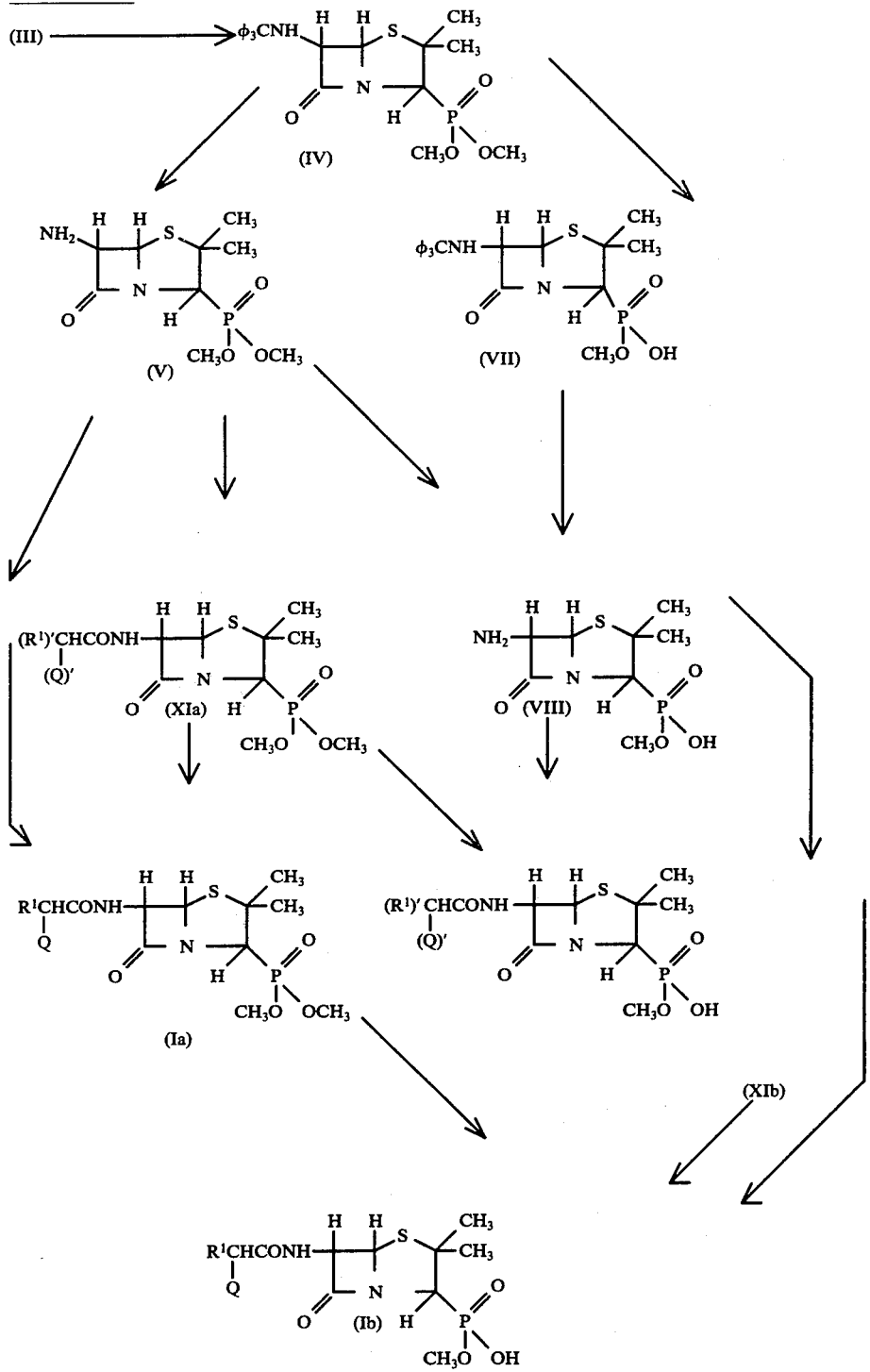

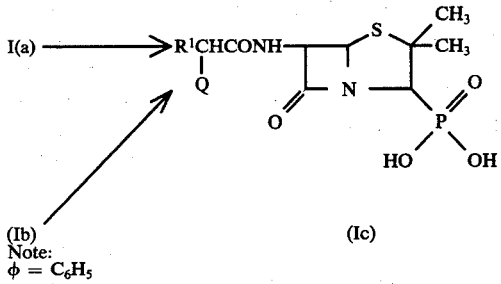

-continued (Ib)
Note:
φ = C₆H₅

The synthesis of the compounds of the invention as described above starts with the well-known intermediate 6-aminopenicillanic acid (6-APA). 6-APA is converted to 6-triphenylmethylaminopenicillanic acid by methods well known in the art, such as by reaction with chlorotriphenylmethane or the like. The 6-triphenylmethyl group in 6-triphenylmethylaminopenicillanic acid serves as a 6-amino protecting group in the subsequent reaction steps, as outlined above, and is removed at the appropriate step to allow acylation of the 6-aminopenam-3-phosphonates as also shown above.

6-Triphenylmethylaminopenicillanic acid has now been found to undergo a novel reaction in the presence of lead tetraacetate to provide the novel intermediate 6-triphenylmethylamino-2,2-dimethyl-3-acetoxypenam (XIII). The novel reaction with lead tetraacetate is carried out in a reaction-inert organic solvent, optionally in the presence of a tertiary amine such as pyridine, and at a temperature in the range of about −30° C. to 80° C. Examples of reaction-inert solvents which may be employed to carry out this novel process are N,N-dimethylformamide, N,N-dimethylacetamide, benzene, toluene, xylene, acetone, methyl ethyl ketone, methyl isobutyl ketone, ethyl acetate, butyl acetate, chloroform, dichloromethane and the like. Preferred reaction-inert solvents for the novel lead tetraacetate reaction are N,N-dimethylformamide and benzene.

While it is advantageous to carry out said lead tetraacetate reactions under anhydrous conditions, rigorous exclusion of moisture is not essential since small amounts of water present will be consumed by the lead tetraacetate reagent. It is also preferred to carry out the reaction in the presence of an inert atmosphere such as that provided by the presence of nitrogen, argon or helium; however, the use of such an inert atmosphere is not an essential condition. Ordinarily, the lead tetraacetate reagent is used in excess of the theoretically-required amount to remove any water remaining in the reaction mixture, or formed as by-product, and fo ensure substantial completion of the reaction. The 3-acetoxypenam products of the novel lead tetraacetate reaction are isolated by standard methods well known to those skilled in the art. For example, the reaction mixture may be filtered to remove insoluble material, and the filtrate washed with an aqueous solution of a neutralizing agent such as sodium hydrogen carbonate. Excess neutralizing agent is removed by water washing and the organic layer is dried and solvent removed by evaporation. The resulting crude product may then be further purified by column chromatography or other methods known in the art.

The intermediate 6-triphenylmethylamino-2,2-dimethyl-3-acetoxypenam (XIII), thus obtained, may be directly converted to α-triphenylmethylamino5,5-dimethyl-3-thiazoline-2-acetic acid (II), or a salt thereof, by reaction with about 2 equivalents of an alkali such as sodium hydroxide or potassium hydroxide in an aqueous medium. This step is preferentially carried out under alkaline hydrolysis conditions at a temperature in the range of about 0° to 100° C. It is also advantageous, but not essential, to employ an organic cosolvent in this process. Co-solvents which can be employed are those which are miscible with water and will serve to dissolve the starting penam compound (XIII). Typical examples of co-solvents which can be used are acetone, lower alkanols, such as methanol and ethanol; ethylene glycol; mono- and di(lower alkyl)ethers of ethylene glycol such as 2-methoxyethanol and 1,2-dimethoxyethane; tetrahydrofuran; dioxane and acetonitrile. The reaction has been found to proceed through the novel intermediate (XIV), depicted below, to form said intermediate (II).

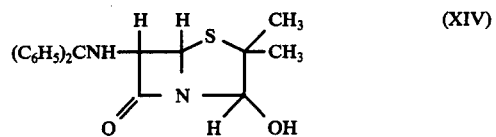

Alternatively, of course, said intermediate (XIV) may be isolated and further reacted to form compound (II).

The isolation of the desired intermediate, α-triphenylmethylamino-5,5-dimethyl-3-thiazoline-2-acetic acid is readily accomplished by methods well known to those skilled in the art. For example, when the reaction is carried out in an aqueous medium containing co-solvent tetrahydrofuran, the co-solvent is removed by evaporation and the aqueous concentrate washed with ether to remove non-acidic by-products. The aqueous layer is chilled and the precipitate that forms is removed and washed thoroughly to obtain the carboxylate salt. This may be dissolved in water, acidified to effect precipitation of the desired acid (II) which can then be isolated by filtration.

The next step in the synthesis of the preferred compounds of the present invention is the production of the novel intermediate α-triphenylmethylamino-5,5-dimethyl-4-(O,O-dimethylphosphono)thiazolidine-2-acetic acid (III) or the salts thereof by the addition of the commercially available compound dimethyl phosphite to the above described 3-thiazoline (II), or a salt thereof. The reaction to form compound (III) may be carried out in the presence of a reaction-inert solvent or may employ an excess of the dimethyl phosphite reagent as solvent. The use of excess dimethyl phosphite is desirable, even when a reaction-inert solvent is employed, to effect completion of the reaction with the more valuable intermediate (II). It is preferred to carry out this process to form novel intermediate (III) at a temperature in the range of about 25° to 80° C. Reaction-inert solvents which may be utilized include dichloromethane, chloroform, ethyl ether, tetrahydrofuran, benzene, toluene, ethyl acetate and the like. Isolation of intermediate (III) is readily accomplished by standard methods, well known in the art.

A key step in the synthesis of the novel compounds of the invention is formation of the β-lactam ring to obtain novel 6-triphenylmethylamino-2,2-dimethylpenam-3-phosphonates such as is shown in Flow Sheets I and II above. The above described intermediate (III) is employed to obtain the preferred novel intermediate (IV), 6-triphenylmethylamino-2,2-dimethyl-3-(O,O-dimethylphosphono)penam. This reaction has been found to take place by reacting intermediate (III) or a salt thereof in the presence of a suitable cyclizing agent. By "suitable cyclizing agent", is meant any of the cyclizing agents known in the art that will react with intermediate (III) or a salt thereof to provide intermediate (IV).

Examples of said suitable cyclizing agents are the 1,3-disubstituted carbodiimides such as 1,3-diisopropylcarbodiimide, 1,3-dicyclohexylcarbodiimide and 1-(3-dimethylaminopropyl)-3-ethylcarbodiimide hydrochloride; alkoxyacetylenes, such as methoxyacetylene and ethoxyacetylene; N-ethoxycarbonyl-2-ethoxy-1,2-dihydroquinoline; di(lower alkyl)chlorophosphonates, each lower alkyl having from one to four carbon atoms; trichloroacetonitrile; trifluoroacetonitrile and the like. Preferred cyclizing agents are 1,3-diisopropylcarbodiimide, 1,3-dicyclohexylcarbodiimide and 1-(3-dimethylaminopropyl)-3-ethylcarbodiimide hydrochloride. Especially preferred is 1,3-diisopropylcarbodiimide.

The ring closure reaction is ordinarily carried out in the presence of a reaction-inert solvent such as dichloromethane, chloroform, 1,2-dichloroethane, benzene, toluene, acetonitrile, tetrahydrofuran, ethyl ether, ethyleneglycol dimethyl ether, diethyleneglycol dimethyl ether, N,N-dimethylformamide, N,N-dimethylacetamide, acetone, methyl ethyl ketone, methyl isobutyl ketone, water and the like. The reaction takes place, to a greater or lesser extent, over a broad range of temperature; that is, from about −50° C. to temperatures of 80° C. or even higher. When contemplating the optimum temperature range for carrying out this reaction step, one must take into consideration that the reaction will proceed more rapidly at the higher end of the above-mentioned temperature range but at the same time higher temperatures tend to favor unwanted side reactions. For these reasons the temperature range of about 0° to 40° C. is preferred for closing the β-lactam ring to obtain intermediate (IV).

As is indicated in Flow Sheet II, the synthesis of compounds of formula (I) may proceed by alternate paths starting with compound (IV). In proceeding next to provide 6-amino-2,2-dimethyl-6-(O,O-dimethylphosphono)penam, (V), the triphenylmethyl 6-amino protecting group is removed by treatment of the said compound of formula (IV) with acid, and a wide variety of acidic reagents and conditions known in the art for removal of the triphenylmethyl group are operable in this process. For example, it is possible to use a sulfonic acid, such as methanesulfonic acid, benzenesulfonic acid or p-toluenesulfonic acid; an anhydrous hydrohalic acid, such as hydrogen chloride or hydrogen bromide; or an alkanoic acid, such as acetic acid, propionic acid, chloroacetic acid, trifluoroacetic acid and the like. The reaction is normally carried out by dissolving the starting material in an appropriate solvent and adding about two molar equivalents of the acid reagent, at or above ambient temperature. Reaction is complete within about one hour, and the product is present in the reaction medium in the form of the acid-addition salt corresponding to the acid reagent used. A solvent should be chosen which will dissolve the starting penam, and examples of solvents which find use are: ethers, such as diethyl ether, tetrahydrofuran, dioxane and 1,2-dimethoxyethane; chlorinated hydrocarbons, such as chloroform, methylene chloride and 1,2-dichloroethane; lower aliphatic ketones such as acetone, methyl ethyl ketone and methyl isobutyl ketone; esters, such as ethyl acetate and butyl acetate; hydrocarbons, such as hexane, cyclohexane and benzene; and lower alkanols, such as methanol, ethanol and butanol. Although it is common to use about two molar equivalents of acid in this process, only one molar equivalent is necessary when either the reaction is carried out in the presence of one molar equivalent of water, or the acid is introduced as a monohydrate. However, as will be realized by one skilled in the art, the product from this reaction should not be exposed to an excess of acid for prolonged periods, since in this case there is a danger of destroying the β-lactam system. A particularly convenient mode of operation for this process, is to choose an acid-solvent system such that the starting material is soluble, but from which the acid addition salt, generated during the reaction, precipitates as it is formed. It can then be recovered by filtration at the end of the reaction. When using the combination of p-toluenesulfonic acid in acetone, the p-toluenesulfonate salt of the product often precipitates.

Alternatively compound (IV) may be used in a process for the production of a compound of formula (VII), 6-triphenylmethylamino-2,2-dimethyl-3-(O-methylphosphono)penam, and the salts thereof, which comprise the step of reacting said compound (IV) under suitable hydrolysis or dealkylation conditions. Said compound of formula (VII) may then be reacted under suitable acidic conditions to remove the triphenylmethyl amino protecting group by one of the above described procedures for obtaining said compound (V), to afford the compound (VIII) or a salt thereof.

Compounds of (V) and (VIII) are each represented by the formula

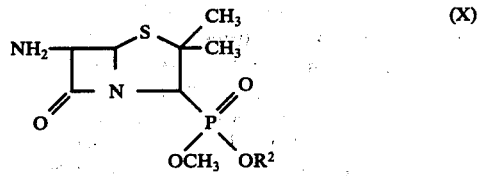

(X)

wherein R² is hydrogen or methyl.

Said compounds of formula (X), or a salt thereof, may be acylated by any of the methods known in the art for acylating 6-APA, the carboxylate salt or the functional derivatives such as the esters thereof. The acylation is carried out by reacting said compound (X) with a suitable organic acylating agent in an appropriate solvent system to obtain compounds of the formulae (Ia), (Ib), (VI), (XI) and (XII) as shown above in Flowsheets I and II.

Any acylating agent which introduces the radical

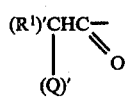

at the 6-amino group of compound (X) is suitable for the purposes of this application. In said radical, $(R^1)'$ is $R^1$ or is phenyl monosubstituted by a member selected from the group consisting of protected aminomethyl and azidomethyl; $(Q)'$ is Q or is a member of the group consisting of protected amino and azido; provided that when $(R^1)'$ is phenoxy or phenyl monosubstituted by a member selected from the group consisting of aminomethyl, protected aminomethyl and azidomethyl, $(Q)'$ is hydrogen; $R^1$ is selected from the group consisting of phenyl, phenoxy, 1,4-cyclohexadienyl, thienyl and phenyl monosubstituted by a member selected from the group consisting of hydroxy, and aminomethyl, and Q is selected from the group consisting of hydrogen, amino, carboxy and sulfo; provided that:

when $R^1$ is selected from the group consisting of phenoxy and phenyl monosubstituted by aminomethyl, Q is hydrogen;

when Q is carboxy, $R^1$ is selected from the group consisting of phenyl and thienyl;

and when Q is sulfo, $R^1$ is phenyl.

One such class of suitable organic acylating agent commonly used is the acid halides, such as the acid chlorides. In a typical acylation procedure, approximately one molar equivalent of an acid chloride is added to a solution of the said compound of formula (X), or a salt thereof, dissolved in a solvent such as a chlorinated hydrocarbon; for example, chloroform or methylene chloride; an ether, for example, tetrahydrofuran or 1,2-dimethoxyethane; an ester, for example, ethyl acetate or butyl acetate; a lower aliphatic ketone, for example, acetone or methyl ethyl ketone; or a tertiary amide, for example, N,N-dimethylformamide or N-methylpyrrolidone; at a temperature in the range from about −40° C. to about 30° C., and preferably from about −10° C. to about 10° C., optionally in the presence of an acid-binder, e.g., triethylamine, pyridine or sodium bicarbonate. The reaction is complete within a short period, i.e., approximately one hour, and the product is isolated by techniques well known in the art, having full regard for the sensitive nature of the penam moiety of the product. For example, the reaction mixture is evaporated to dryness and a water-immiscible organic solvent and water are added. In those cases where the product precipitates, it is filtered off. If the product does not precipitate, then the pH of the aqueous phase is adjusted to an appropriate value and the phase containing the product is evaporated. The crude product thus obtained can be purified further if desired. When $R^2$ is hydrogen, it is convenient to employ a tertiary amine salt, for example, the triethylamine salt, of the compound of formula (X) wherein $R^2$ is hydrogen. An alternate procedure useful for the acylation of a compound of formula (X) with acid halides involves the use of an aqueous solvent system. In this procedure, which approximates the Schotten-Baumann procedure, the acid halide is added to a solution of the starting material in water, or a mixture of water and another inert solvent, at, or slightly below, ambient temperature, with the pH of the solvent being maintained within the range from about 6.0 to about 9.0 before, during, and after the addition. At the end of the reaction, the product can often be induced to precipitate by adjustment of the pH. Alternatively, it can be extracted into a water-immiscible solvent, which is then evaporated to dryness.

Another such class of suitable organic acylating agents which find use are the mixed anhydrides such as those formed by reacting the carboxylic acid containing the desired 6-acyl group, or a salt thereof, with a loweralkyl chloroformate or pivaloyl chloride. In the former case, for example, a carboxylate salt of the appropriate carboxylic acid is treated with about one molar equivalent of a lower-alkyl chloroformate in a reaction-inert, aprotic organic solvent, at a temperature in the range from about −20° C. to about 20° C. and preferably at about 0° C. Appropriate salts for this process are alkali metal salts, such as sodium and potassium salts, and tertiary amine salts, such as triethylamine, tributylamine, N-ethylpiperidine, N,N-dimethylaniline, N-methylmorpholine and pyridine salts; and appropriate solvents are, for example chloroform, methylene chloride, acetonitrile, acetone, tetrahydrofuran, dioxane and N,N-dimethylformamide. The mixed carboxylic-carbonic anhydride thus formed is usually used in situ to acylate the said compound of formula (X). This is normally carried out by mixing solutions of the preformed mixed anhydride and the compound of formula (X). When $R^2$ is hydrogen, it is particulary convenient to employ a tertiary amine salt, for example the triethylamine salt, of the compound of formula (X). The acylation is normally conducted at a temperature in the range from about −30° C. to about 20° C., and preferably at about −10° C., and is usually complete within a few hours. In most instances, the mixed anhydride and the compound of formula (X) are contacted substantially in a 1:1 molar ratio. The product is usually isolated by evaporating the reaction mixture to dryness, and then adding a water-immiscible organic solvent and water. By careful adjustment of the pH, the product sometimes precipitates. In other cases the phases are separated, and the product-containing phase is evaporated to dryness. The crude product so obtained can be purified further if desired.

A still further variation which is suitable for the acylation of compounds of formula (X) comprises contacting the said compound of formula (X) with the appropriate carboxylic acid in the presence of certain agents known in the art for forming peptide bonds. Such agents include carbodiimides, for example, dicyclohexylcarbodiimide and 1-ethyl-3-(3-dimethylaminopropyl)-carbodiimide hydrochloride, alkoxyacetylenes, for example methoxyacetylene and ethoxyacetylene, and N-ethoxycarbonyl-2-ethoxy-1,2-dihydroquinoline. The reaction is carried out in an appropriate solvent, i.e., one which will serve to dissolve the reactants, and does not adversely interact with the starting materials or the product, for example acetonitrile, N,N-dimethylformamide and N-methylpyrrolidone.

When the acylation is carried out with compound (X) wherein $R^2$ is hydrogen, the hydrogen substituent located at $R^2$ can successfully be replaced by a trialkylsilyl substituent. Said trialkylsilyl substituent is then removed and replaced by hydrogen at the end of the acylation simply by brief exposure of the product to a protic solvent system such as water or a lower-alkanol, for example, methanol or ethanol. By virtue of the ready availability of the starting materials, the trimethylsilyl group is a preferred member. It can be introduced into the starting penam of formula (X) wherein $R^2$ is hydrogen by methods well known in the art, such as, for example, using trimethylchlorosilane or N-trimethylsilylacetamide, as discussed by Birkofer and Ritter in Angewandte Chemie (International Edition in English), 4, 417–418 and 426 (1965). Conditions must be chosen, however, which are compatible with the β-lactam group of the penam nucleus. Also operative are the silylated derivatives formed by interaction of the said compound of formula (X) wherein $R^2$ is hydrogen with dichlorodi(lower-alkyl)silanes. The silylation step is carried out by methods known in the art (for example, German Pat. No. 1,933,187). After the acylation reaction, the silyl group is removed by treatment with a protic solvent, such as water or a lower-alkanol, for example methanol or ethanol.

Further, in the preparation of compounds of the formulae (Ia), (Ib) and (XII) wherein Q is carboxy and $R^1$ is selected from the group consisting of phenyl and thienyl, the mono-acid chloride of the appropriate 2-substituted malonic acid precursor is a suitable acylating agent. Preparation and use of the said mono-acid chlorides are taught in Belgian Pat. No. 788,928.

In the preparation of compounds of the formulae (Ia), (Ib), (VI) and (XII) wherein $R^1$ is phenyl and Q is sulfo, a suitable acylating agent is obtained for example, by reacting a tertiary amine salt of 2-sulfo-2-phenylacetic acid, e.g. the bis-triethylamine salt with a lower alkyl chloroformate such as ethyl chloroformate to obtain a mixed carbonic-carboxylic acid anhydride (see Nicolaus, et al., Ann. di Chim. (Rome), 53, 14 (1963). The mixed anhydride is then reacted with a compound of formula (X) as described above.

In the preparation of compounds of the formulae (Ia), (Ib), (VI) and (XII) wherein Q is amino and those wherein $R^1$ is aminomethylphenyl, said amino and aminomethyl groups present in the starting carboxylic acid must be protected prior to carrying out the acylation. A particularly valuable acylation procedure comprises the use of the acid chloride hydrochloride of the precursor acid. The acid chloride hydrochlorides are prepared, and the acylation is conducted, by the methods described in U.S. Pat. No. 3,140,282 for the preparation of 2-amino-2-phenylacetyl chloride hydrochloride and the subsequent acylation of 6-amino-penicillanic acid.

Another method for providing compounds of the formula (Ia), (Ib), (VI) and (XII) wherein Q is amino and those wherein $R^1$ is aminomethylphenyl is to protect said amino or aminomethyl group in the starting carboxylic acid prior to activation of the carboxy group of the said acid. After the amino group is protected, the carboxy group is activated and the acylation carried out by one of the above described methods to obtain an intermediate compound of formula (XI), or a salt thereof. Upon further reacting said compound of formula (XI) containing said protected amino or protected aminomethyl group, compounds of the formulae (Ia), (Ib), (VI) and (XII) are obtained. Compounds of the formulae (Ia) upon further reacting under suitable hydrolysis or dealkylation conditions as described below afford the corresponding compounds of formula (Ib). Compounds of formula (Ia), (Ib) and (XII) can, in turn be converted to the corresponding 3-phosphonopenams of formula (Ic) by methods also described below.

A wide variety of protecting groups known in the art for protecting amino groups during peptide synthesis can be used for protecting the above mentioned amino and aminomethyl groups. See, for example, Schroder and Lubke, "The Peptides", Academic Press, New York, N. Y., Volume I, 1965, pp. 3–51 and "Peptides", edited by Zervas, Pergamon Press, New York, N. Y., 1966, pp. 3–118 Examples of amino protecting groups which may be introduced are benzyloxycarbonyl, p-nitrobenzyloxycarbonyl, p-toluenesulfonyl, trityl, benzyl, dibenzyl, benzylsulfonyl, trifluoroacetyl, chloroacetyl, formyl, o-nitrophenylsulfenyl, o-nitrophenoxyacetyl, and enamines formed by interaction of the starting amino acid with a β-dicarbonyl compound. Groups which have been found to be particularly suitable are the benzyloxycarbonyl group, use of which is taught by Doyle et al., J. Chem. Soc., 1440 (1962), and the enamines formed by interaction of the starting amino acid with a β-dicarbonyl compound as taught by Dane and Dockner, Angewante Chemie (International Edition in English), 3, 439 (1964) and in Chemische Berichte, 98, 789 (1965). Examples of useful β-dicarbonyl compounds are the esters and amides of acetoacetic acid. Prepared amino protecting groups are those obtained with the methyl and ethyl esters of acetoacetic acid which readily react with said amino or aminomethyl groups to afford enamines of the formula

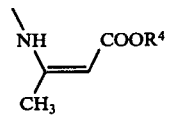

wherein $R^4$ is methyl or ethyl. Amino acids wherein the amino group is protected with the above enamine moiety may readily be activated as described above to provide suitable acylating agents which react with compounds of the formula (X) or a salt thereof to obtain a compound of formula (XI). The protecting group is subsequently removed under mild hydrolytic conditions to obtain compounds of the formula (Ia), (Ib), (VI) and (XII).

Still other suitable organic acylating agents useful for obtaining said compounds of formula (XI) are provided by the α-azido carboxylic acids and the 2-(azidomethylphenyl)acetic acids such as 2-azido-2-phenylacetic acid and 2-(2-azidomethylphenyl)acetic acid. When these azido acids are activated as described above and reacted with a compound of the formula (X) or a salt thereof, the corresponding intermediates of formula (XI) are obtained wherein $(R^1)'$ is phenyl and $(Q)'$ is azido or wherein $(R^1)'$ is phenyl substituted by azidomethyl and $(Q)'$ is hydrogen. Upon further reacting of said compounds of formula (XI) containing said azido or azidomethyl groups, as for example with hydrogen in the presence of a noble metal catalyst, the corresponding amino or aminomethyl compounds of the formulae (Ia), (Ib) and (XII) are obtained.

It will be appreciated by one skilled in the art that not all the suitable organic acylating agents discussed above are equally effective or convenient in all cases for the acylation of a compound of formula (X). The relative effectiveness of a particular variation will differ according to a number of factors, such as, for example, the precise structure of the said compound of formula (X), the availability of starting materials, the scale of the reaction and, in particular, the structure and reactivity of the acyl group being introduced. In practice, one skilled in the art will select the most appropriate variation in each case, having full regard for the relevant factors.

Penam compounds of the formulae (Ia), (IV), (V), (XIa) and (XV) which contain the -3-(O,O-dimethylphosphono) group have been found to react to provide the corresponding 3-(O-methylphosphono)penams of the formulae (Ib), (VII), (VIII), (XIb), and (XVI), respectively.

Methods which may be employed to obtain the desired 3-(O-methylphosphono)penams include hydrolysis methods known in the art and various dealkylation procedures such as those which utilize halide salts of alkali metal as, for example, sodium chloride, lithium bromide, potassium bromide, sodium iodide, lithium iodide and the like. Especially useful are the lithium iodide reagent (see Fieser et al., "Reagents for Organic Synthesis", John Wiley and Sons, Inc., New York, Vol. I, 1967, p. 615 ff. and references cited therein), and the reactions with trimethylhalosilanes such as trimethylchlorosilane and trimethylbromosilane, followed by hydrolysis of the resulting silyl phosphonates as described by Rabinowitz, *Journal of Organic Chemistry*, 28, 2975 (1963); Baer, et al., *Canadian Journal of Chemistry*, 51, 104 (1973) and Paulsen, et al., *Chemische Berichte*, 108, 1732 (1975).

The trimethylhalosilane-hydrolysis procedure is known in the art to afford the corresponding phosphonic acid compounds, and it has not been reported to give, e.g., O-methylphosphono compounds. Thus it would be expected to favor the -3-(phosphono)penams. This procedure can also be employed to convert 3-(O-methylphosphono)penams or their salts to the corresponding -3-(phosphono)penams.

Use of the lithium iodide reagent is preferred for the conversion of compounds of the formula (Ia), (IV), (V), (XIa) and (XV) and salts thereof, to the corresponding 3-(O-methylphosphono)penams of the formulae (Ib), (VII), (VIII), (XIb) and (XVI), respectively, and the salts thereof. The reaction with the preferred lithium iodide reagent is carried out under anhydrous conditions in the presence of an organic solvent. Solvents which may be used include, for example, pyridine, the picolines, such as 2-methylpyridine, the lutidines, such as 2,6-dimethylpyridine, the collidines, such as 2,4,6-trimethylpyridine, N,N-dimethylformamide and the like. Preferred as solvent for this reaction is pyridine. The reaction may be carried out with satisfactory results at temperatures in the range of about −30° C. to 100° C.

In carrying out the above reaction, a large excess of the lithium iodide reagent is favored, and the use of 4 moles of lithium iodide per mole of 3-(O,O-dimethylphosphono)penam affords especially good results. After the reaction has been allowed to proceed to substantial completion, the desired product may be isolated by various procedures which will be obvious to those skilled in the art, such as, for example, removal of the bulk of the reaction solvent by evaporation under reduced pressure, after which the residue may be partitioned between water and a water immiscible solvent such as ether. The solvent is discarded and the solvent wash repeated, if necessary, to remove the last traces of the reaction solvent, e.g., pyridine. The aqueous phase is then acidified to precipitate the desired -3-(O-methylphosphono)penam which may be further purified.

The lithium iodide reagent may also be employed to obtain -3-(phosphono)penams (Ic) from the corresponding 3-(O-methylphosphono)penams (Ib), (XII, $R^2$ = hydrogen). In carrying out this reaction the acidic hydrogen present in the starting -3-(O-methylphosphono)penam may be protected by reaction with a silylating agent is the presence of a tertiary amine and the resulting 3-(O-trimethylsilyl-O-methylphosphono)penam subjected to the above described reaction with lithium iodide to obtain an intermediate -3-(O-trimethylsilylphosphono)penam. The latter intermediate may then be hydrolyzed to remove the silyl group and provide 3-phosphono penam of formula (Ic). Alternatively, the latter compounds can be similarly obtained by reacting the -3-(O,O-dimethylphosphono)penams of formulae (Ia) and (XII, $R^2$ = methyl) with lithium iodide and a silylating agent in the presence of a tertiary amine and the subsequent treatment with water.

Thus, in the preferred method for obtaining compounds of formula (Ic), compounds of formula (XII) wherein $R^2$ is hydrogen or methyl are reacted with lithium iodide and a silylating agent in the presence of a tertiary amine which serves as an acid binding agent, and subsequent treatment with water. The term "tertiary amine" is illustrated by any of the well-known compounds such as triethylamine, N-ethylpiperidine, N-methylmorpholine, N-ethylpyrrolidine, N,N-dimethylaniline, pyridine, the picolines, lutidine, quinoline and isoquinoline known in the art as capable of forming amine salts. Preferred tertiary amines are those which can also serve as solvent for the reaction. An especially preferred tertiary amine is pyridine for reasons of economy and efficiency. By the term "silylating agent" is meant any of the well-known agents such as those discussed in "*Silylation of Organic Compounds*", Pierce Chemical Company, Rockford, Illinois and in U.S. Pat. No. 3,499,909, which are capable of reacting under anhydrous conditions with carboxylic and sulfonic acid groups to form silyl esters and with primary and secondary amines to form silylated amines; and such silyl esters and silylated amines are capable of regenerating said carboxylic acids and sulfonic acids and said amines upon treatment with water. Examples of such silylating agents are the trialkylhalosilanes such as trimethylchlorosilane, triethylchlorosilane, tri-n-propylbromosilane, tri-n-butylchlorosilane, methyldiethylchlorosilane and dimethylethylchlorosilane; and hexamethyldisilazane, dimethyldichlorosilane, bromomethyldimethylchlorosilane, phenyldimethylbromosilane, benzylmethylethylchlorosilane, phenylethylmethylchlorosilane, triphenylchlorosilane, triphenylfluorosilane, tri-o-tolylchlorosilane, tri-p-dimethylaminophenylchlorosilane, N-ethyltriethylsilylamine, hexaethyldisilazane, triphenylsilylamine, tri-n-propylsilylamine, tetraethyldimethyldisilazane, tetramethyldiethyldisilazane, tetramethyldiphenyldisilazane, hexaphenyldisilazane, hexa-p-tolyldisilazane, etc., and mixtures of these. The same effect is produced by hexaalkylcyclotrisilazanes or octaalkylcyclotetrasilazanes. Other suitable silylating agents are silylamides and silylureides, such as a trialkylsilylacetamide and a bis-trialkylsilylacetamide as is disclosed in U.S. Pat. No. 3,499,909. However, the lower trialkylchlorosilanes are preferred, and especially preferred is trimethylchlorosilane because of its ready availability, efficiency and economy.

In carrying out the preferred method for preparing compounds of formula (Ic), a large excess of both lithium iodide and said silylating agent relative to the starting material of formula XII are favored and 4 to 8 moles of lithium iodide and 3 to 8 moles of said silylating agent afford especially good results. The amount of tertiary amine, such as pyridine, should be in excess of the silylating agent and from about 4 to 20 moles or more per mole of compound (XII) are favored. While the reaction may be carried out over a wide range of temperature to provide compounds of formula (Ic), temperatures in the range of about −30° to 100° C. are preferred.

Any of the above reactions employing lithium iodide reagent ordinarily reach substantial completion at room temperature within a few hours. Of course, more time will be required when a temperature at the lower end of the preferred range of temperature is employed and less time will be required at the upper end of said temperature range. For example, at −30° C. the reaction may require a few days, while at 100° C. the reaction will ordinarily be complete within a few minutes.

In the above mentioned reactions involving lithium iodide and a silylating agent in the presence of a tertiary amine, the compounds of formula (Ic) are obtained by subsequent treatment of the reaction mixture with water. Said treatment with water ordinarily requires only a few minutes exposure to a molar excess of water and comparable results are obtained when said water is acidic, alkaline or neutral. It is usually sufficient, for example, to expose the reaction mixture to water during partitioning between water and a water immiscible solvent such as chloroform, methylene dichloride, ethyl acetate and the like.

The compounds of formula (Ic) may be isolated either in the form of the free -3-phosphonopenam or in the form of a salt such as the sodium, potassium or calcium salt. Alternatively, in those cases where there is an amino group attached to the $R^1$ or Q substituent of said compound of formula (Ic), the product may be isolated in the form of an acid addition salt, such as the hydrochloride salt or hydrobromide salt, or as a zwitterion by precipitation at the isoelectric point.

Nuclear magnetic resonance ($^1$H-nmr) evidence indicates that the stereochemistry of the prevailing isomers of the compounds of the invention is the same as that of the naturally occurring penicillins such as the well-known Penicillin G, see for example Manhas and Bose, "Synthesis of Penicillin, Cephalosporin C and Analogs", Marcel Dekker, Inc., New York, N.Y., 1969, pp. 26–35, and references cited therein. However, all isomers of the said compounds of the invention are within the scope and purview of the instant invention.

A characteristic feature of the compounds of the formulae (VII), (VIII), and (XIb) and most compounds of the formula (I) is their ability to form salts. By virtue of the acidic nature of all of these except those of formula (Ia), the said compounds have the ability to form salts with basic agents, and these salts, referred to generically as "phosphonate" salts in this specification are to be considered within the scope of this invention. The salts can be prepared by standard techniques, such as contacting the acidic and basic components, usually in a 1:1 molar ratio, in an aqueous, non-aqueous or partially aqueous medium, as appropriate. They are then recovered by filtration, by precipitation with a non-solvent followed by filtration, by evaporation of the solvent, or, in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate; sodium 2-ethylhexanoate and potassium 2-ethylhexanoate.

Further, when Q is selected from the group carboxy and sulfo in each of the compounds of formulae (I) and (XII) they have the ability to form the respective carboxylate and sulfonate salts. These salts, which can be prepared in exactly the same manner and using the same basic agents, as described above for the phosphonate salts, are also within the purview of this invention. Clearly, certain of the compounds of formulae I can form mono-, di- and tri-salts. When considering di-salts and tri-salts, the cationic moieties can be the same or different.

The intermediates of formulae II and III also have the ability to form carboxylate salts which can be of use in their isolation and purification. These salts can also be prepared in the same manner and using the same basic agents as described above for the phosphonate salts, and are within the scope and purview of the invention.

The compounds of formulae (I) and (XII) which contain an amino group, and the intermediates of formula (X) have the ability to form acid-addition salts. Said acid-addition salts are also to be considered as being within the scope of this invention. Examples of acid-addition salts which are particularly valuable are: hydrochloride, hydrobromide, phosphate, perchlorate, citrate, tartrate, pamoate, glutarate, benzoate, sulfate, lactate, and arylsulfonate salt.

When therapeutic use in mammals is being contemplated for a salt of a compound of the instant invention, it is of course essential to use a pharaceutically-acceptable salt. However, other salts are useful for a variety of other purposes; such as, for example, isolating and purifying individual compound, changing the solubility characteristics of an individual compound, and for interconverting pharmaceutically-acceptable salts with their non-salt counterparts.

The compounds of formula I and the pharmaceutically acceptable salts thereof are active against a variety of bacteria, especially gram positive bacteria such as *Staphlococcus aureus, Streptococcus pyogenes, Streptococcus equis* and *Streptococcus zoobacter*. The compounds are especially useful as animal feed supplements to promote growth. For this purpose one or more of said compounds is added at a low level to the diet of healthy animals, both ruminant and non-ruminant, such that the animal receives the product over an extensive period of time at a daily dosage of from about 5 mg./kg. of body weight to about 500 mg./kg. of body weight. However, in general, it will be found that a dosage in the range of about 10 mg./kg. of body weight to about 100 mg./kg. of body weight will suffice. When employed in this manner, especially over a major portion of the animals active growth period, an acceleration in the rate of growth and improved feed efficiency (the number of pounds of feed required to produce a pound gain in weight). Included in these two classes of animals are poultry such as chickens, turkeys and ducks; cattle, sheep, dogs, cats, swine, rats, mice, horses, goats, mules, rabbits, mink, etc. The beneficial effects in growth rate and feed efficiency are over and above what is normally obtained when complete nutritous diets containing all the nutrients, vitamins, minerals and other factors known to be required for the maximum healthy growth of such animals. The animals thus attain market size sooner and on less feed.

When used for such purposes, these novel compounds are administered orally. The preferred methods of administration are by mixing with animal feeds, the preparation of feed concentrates and supplements and dilute solutions or suspensions, e.g., a 0.2 percent solution, for drinking purposes.

In some instances, the degree of response may vary with respect to the sex of the animals. Said compounds and salts of formula I may, of course, be administered in one component of the feed or they may be blended uniformly throughout a mixed feed; alternatively, as noted above, they may be administered in an equivalent amount via the animal's water ration. It should be noted that a variety of feed components may be of use in the nutritionally balanced feeds. Any animal feed composition may be prepared to comprise the usual nutritional balance of energy, proteins, minerals and vitamins together with one or more of said compounds and salts of formula I. Some of the various components are commonly grains such as ground grain and grain by-products; animal protein substances, such as meat and fish byproducts; vitaminaceous mixtures, e.g., vitamin A and D mixtures, riboflavin supplements and other vitamin B complexes; and bone meal, limestone and other inorganic compounds to provide minerals.

The relative proportions of the present compounds in feeds and feed concentrates may vary somewhat, depending upon the compound, the feed with which they are employed and the animal consuming the same. These substances are advantageously combined in such relative proportions with edible carriers as to provide pre-mixes or concentrates which may readily be blended with standard nutritionally balanced feeds or which may be used themselves as an adjunct to normal feedings.

In the preparation of concentrates a wide variety of carriers, including the following: soybean oil meal, corn gluten meal, cotton seed oil meal, sunflower seed meal, linseed oil meal, cornmeal, limestone and corncob meal can be employed. The carrier facilitates uniform distribution of the active materials in the finished feed with which the concentrate is blended. The concentrate may be surface coated, if desired, with various proteinaceous materials or edible waxes, such as zein, gelatin, microcrystalline wax and the like to provide a protective film which seals in the active ingredients. It will be appreciated that the proportions of the drug preparation in such concentrates are capable of wide variation since the amount of active materials in the finished feed may be adjusted by blending the appropriate proportion of concentrate with the feed to obtain the desired degree of supplementation. In the preparation of high potency concentrates, i.e., premixes, suitable for blending by feed manufacturers to produce finished feeds or concentrates of lower potency, the drug content may range from about 0.5 g. to 50 g. per pound of concentrate. The high potency concentrates may be blended by the feed manufacturer with proteinaceous carriers, such as soybean oil meal, to produce concentrated supplements which are suitable for direct feeding to animals. The proportion of the drug in these supplements may vary from about 0.2 to 10 g. per pound of supplement. A particularly useful concentrate is provided by blending 5 g. of drug with 1 pound of limestone or 1 pound of limestone-soybean oil meal (1:1). Other dietary supplements, such as vitamins, minerals, etc. may be added to the concentrates in the appropriate circumstances.

The concentrates described may also be added to animal feeds to produce a nutritionally balanced, finished feed containing from about 50 to about 1000 g. of the herein described compounds per ton of finished feed. In the case of ruminants, the finished feed should contain protein, fat fiber carbohydrate, vitamins and minerals, each in an amount sufficient to meet the nutritional requirements of the animal for which the feed is intended. Most of these substances are present in naturally occurring feed materials, such as alfalfa hay or meal, cracked corn, whole oats, soybean oil meal, corn silage, ground corn cobs, wheat bran and dried molasses. Bone meal, limestone, iodized salt and trace minerals are frequently added to supply the necessary minerals and urea to provide additional nitrogen.

As is well known to those skilled in the art, the types of diets are extremely variable depending upon the purpose, type of feeding operation, species, etc. Specific diets for various purposes are listed by Morrison in the Appendix of "Feeds and Feeding", the Morrison Publishing Company, Clinton, Iowa, 1959.

In the case of non-ruminant animals, such as hogs, a suitable feed may contain from about 50 to 80 percent grains, 3 to 10 percent animal protein, 5 to 30 percent vegetable protein, 2 to 4 percent of minerals, together with supplementary vitaminaceous sources.

The in vitro activities are determined under anaerobic conditions in the following manner.

Appropriate serial two-fold dilutions of the compounds are mixed with molten brain-heart infusion agar in sterile petri dishes and allowed to solidify.

The bacterial cells (approximately $10^5$–$10^6$ cells) are placed on the top of the agar plate with a Steers replicating device. The plates are incubated at 37° C. in the anaerobic conditions achieved by a Gas Pak (BBL, Cockeysville, Ind.). The M.I.C. (minimal inhibitory concentration) is taken as the lowest concentration of drug which completely inhibits bacterial growth.

The in vitro activities of the sodium salts of 6-(2-phenoxyacetamido)-2,2-dimethyl-3-(O-methylphosphono)penam and 6-(2-phenoxyacetamido)2,2-dimethyl-3-phosphonopenam against the above mentioned Streptococcus and Staplococcus species are summarized below in Table I.

TABLE I

IN VITRO ANTIBACTERIAL DATA
MIC (mcg./ml.) OF COMPOUNDS OF FORMULA (I)

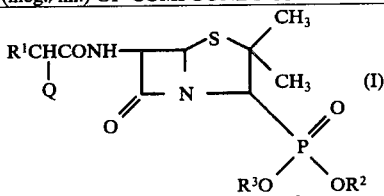

| Test No. | R¹ | Q | R² | R³ | Staph. aureus 01A005 | Staph. aureus 01A006 | Strep. pyogenes 02C203 | Strep. equi. 02I001 | Strep. zoo. 02H001 |
|---|---|---|---|---|---|---|---|---|---|
| 1 | C₆H₅O | H | CH₃ | H | 200 | 200 | >200 | 200 | >200 |
| 2 | C₆H₅O | H | CH₃ | H | 200 | 200 | 200 | 200 | >200 |
| 3 | C₆H₅O | H | CH₃ | H | 200 | 200 | 3.1 | — | >200 |
| 1 | C₆H₅O | H | H | H | 200 | 200 | >200 | >200 | >200 |
| 2 | C₆H₅O | H | H | H | >200 | >200 | 100 | 100 | 100 |
| 3 | C₆H₅O | H | H | H | 200 | 200 | 50 | — | 200 |

Certain of the compounds of this invention have the ability to form solvates (e.g. hydrates), and all such solvates are to be considered within the scope and purview of the invention.

The following examples are provided solely for the purpose of further illustration. Except where noted, infrared (IR) spectra are measured as potassium bromide discs (KBr discs), and diagnostic absorption bands are reported in wave numbers (cm⁻¹). Nuclear magnetic resonance spectra (¹H-nmr) are measured at 60 MHz for solutions in deuterochloroform (CDCl₃), perdeutero dimethyl sulfoxide (DMSO-d₆) or deuterium oxide (D₂O), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

6-(Triphenylmethylamino)penicillanic Acid

To a stirred suspension of 54 g. (0.25 mole) of 6-aminopenicillanic acid and 70 ml. (0.50 mole) of triethylamine in 500 ml. of chloroform (free of ethanol) at room temperature, 70 g. (0.25 mole) of chlorotriphenylmethane was added in portions over a period of a few minutes. Stirring was continued for two days. The volatile components were evaporated under reduced pressure, and the foamy residue taken up in 400 ml. of water. The aqueous mixture was washed twice with 300 ml. portions of diethyl ether, and then brought to pH 4.0 by the monitored addition of 4N hydrochloric acid. Organic matter was extracted with two 300 ml. portions of diethyl ether. The extracts were combined, washed twice with 200 ml. portions of water, once with 200 ml. of a saturated aqueous sodium chloride solution, and dried over anhydrous sodium sulfate. Evaporation of the solvent affords 6-(triphenylmethylamino)penicillanic acid as a yellow foam; yield 95 g. (83%); ¹H-nmr (CDCl₃) ppm (δ):1.4 (s,3,α-CH₃), 1.6 (s,3,β-CH₃), 4.4 (m,3,c-3, C-5, C-6 protons), 7.4 (m,15,C₆H₅).

EXAMPLE 2

6-triphenylamino-2,2-dimethyl-3-acetoxypenam

A solution of 46 g. (0.10 mole) of 6-(triphenylmethylamino)penicillanic acid and 425 ml. of benzene was heated under reflux in an apparatus which includes a Dean-Stark moisture trap. When no further water was collected in the trap, a stream of dry nitrogen was allowed to pass through the solution while it cooled to room temperature. Lead tetraacetate-10% acetic acid (64 g., 0.13 mole) was added in one portion, the mixture was stirred under nitrogen for 15 hours, and then filtered through a pad of diatomaceous earth (Celite). The filtrate was washed twice with 300 ml. portions of half-saturated aqueous sodium hydrogen carbonate, twice with water, and dried over anhydrous sodium sulfate. Evaporation of the volatile components furnished 15 g. of a brown foam. This residue was subjected to chromatography though a column containing 350 g. of silica gel. Eluting the column with chloroform afforded some initial undesired material, but this was followed by fractions containing 6-triphenylmethylamino-2,2-dimethyl-3-acetoxypenam. Evaporation of these combined fractions gave material which was approximately 65% pure; yield 11 g. (15%); ¹H-nmr (CDCl₃) ppm (δ):1.3 (s,3,α-CH₃), 1.5 (s,3,β-CH₃), 2.0 (s,3,COCH₃), 3.3 (d,1,NH), 4.4 (m,2,C-5, C-6 protons), 6.2 (s,1,C-3), 7.4 (m,15,C₆H₅). The product may be crystallized from an ether-methanol mixture.

When the above reaction is carried out, but using N,N-dimethylformamide as solvent in place of benzene and with suitable modification of the above isolation procedure, the title compound is obtained. When the reaction is carried out at 80° C. for 15 minutes using benzene as solvent, or at −30° C. for 120 hours in dichloromethane, the title compound is also obtained.

When one equivalent of pyridine (based on the starting 6-[triphenylmethylamino]penicillanic acid) is employed in the above procedures, the title compound is likewise obtained.

EXAMPLE 3

α-Triphenylmethylamino-5,5-dimethyl-3-thiazoline-2-acetic Acid

A solution of 6.37 g. (0.0135 mole) of 6-triphenylmethylamino-2,2-dimethyl-3-acetoxypenam, 65 ml. of tetrahydrofuran, 13.5 ml. of water, and 13.5 ml. of 2N aqueous sodium hydroxide was stirred at room temperature for 60 hours. The reaction mixture was concentrated under reduced pressure to about one-third of the original volume, and the aqueous concentrate washed three times with 50 ml. portions of diethyl ether. Precipitation occurred during the washing process. After allowing the mixture to stand at 0' C. for 30 minutes, the solids were removed by filtration and washed once with a small portion of ice-water and twice with 20 ml. portions of diethyl ether. The crystalline sodium salt thus obtained was dissolved in a stirred mixture of 30 ml. of water and 50 ml. of dichloromethane and the pH adjusted to 4.0. The organic phase was separated, dried over anhydrous sodium sulfate, and evaporated under reduced pressure to afford nearly colorless crystals of the title compound; yield 3.45 g. (59%); mp. 180°–182° C;¹H-nmr (CDCl$_3$) ppm (δ):1.42 (s,3,CH$_3$), 1.52 (s,3,CH$_3$), 3.96 (d,J$_{5,6}$=5 cps,1,C-6)*, 5.93 (q, J$_{3,5}$=2.7, J$_{5,6}$=5,1C-5)*, 6.98 (d,J=2.7, 1,C-3)*, 7.36 (m,15,C$_6$H$_5$).

*penam numbering

When the above reaction is repeated but using acetone as co-solvent in place of tetrahydrofuran and at a temperature of 0° C. for 200 hours, the title compound is likewise obtained.

Similarly, when the reaction is carried out at 100° C. for one hour using 2-methoxyethanol (methyl Cellosolve) as co-solvent, the title compound is obtained.

EXAMPLE 4

α-Triphenylmethylamino-5,5-dimethyl-3-thiazoline-2-acetic acid via 6-Triphenylmethylamino-2,2-dimethyl-3-hydroxypenam A. 6-Triphenylmethylamino-2,2-dimethyl-3-hydroxypenam To a solution of 1.7g. (0.0036 moles) of 6-triphenylmethylamino-2,2-dimethyl-3-acetoxypenam in 10 ml. of tetrahydrofuran was added 2.0 ml. of 2N sodium hydroxide solution and the resulting mixture was stirred rapidly for 30 minutes at 25° C. Ethyl ether (50 ml.) was then added with stirring and the layers were allowed to separate. The aqueous layer was discarded and the organic layer was washed three times with 2 ml. portions of water, once with saturated aqueous sodium chloride solution, dried over anhydrous sodium sulfate and concentrated in vacuo to obtain 1.6 g. of semisolid foam. The foam was dissolved in 3 ml. of chloroform and chromatographed on 40 g. of silica gel, eluting with chloroform. Seventy fractions, 5 ml. each, were collected. Fractions 5–50 were found to contain starting material and fractions 53–70 were found to contain only one compound, more polar than the starting material upon thin-layer chromatography. Fractions 53–70 were combined and evaporated in vacuo to obtain 250 mg. of 6-triphenylmethylamino-2,2-dimethyl-3-hydroxypenam. ¹H-nmr (CDCl$_3$) ppm (δ): 1.40 (s,3,CH$_3$), 1.44 (s,3CH$_3$), 3.23 (d,1,NH), 4.3 (m, 2,C-5 and C-6), 5.13 (s,1,C-3), 7.17–7.66 (m,15,C$_6$H$_5$).

B. α-Triphenylmethylamino-5,5-dimethyl-3-thiazoline-2-acetic acid, Sodium Salt

To a solution of 210 mg. (0.49 millimoles) of 6-triphenylmethylamino-2,2-dimethyl-3-hydroxypenam in one milliliter of tetrahydrofuran was added 0.25 ml. of 2N sodium hydroxide solution. The resulting mixture was stirred at room temperature for one hour, after which 5 ml. of ether and 0.3 ml. of deuterium oxide were added. The lower, aqueous, layer was removed and concentrated in vacuo to obtain a crystalline residue. To this was added 0.5 ml. of D$_2$O followed by 1 drop of dilute hydrochloric acid to adjust the pH to about 7. The resulting mixture was stirred for several minutes after which the solid material was allowed to settle and the liquid drawn off with a micropipette. The resulting crystals were dried in vacuo, then dissolved in perdeutero-dimethylsulfoxide. The ¹H-nmr spectrum was identical to that of an authentic specimen of the sodium salt of α-triphenylmethylamino-5,5-dimethyl-3-thiazoline-2-acetic acid. ¹H-nmr (DMSO-d$_6$) ppm (δ): 1.22 (s,3,CH$_3$), 1.32 (s,3,CH$_3$), 3.45 (d,1,C-6*) 4.68 (m,1,C-5*), 6.68 (d,1,C-3*), 7.07–7.48 (m,15,C$_6$H$_5$).

penam numbering

EXAMPLE 5

α-Triphenylmethylamino-5,5-dimethyl-4-(O,O-dimethylphospono)-thiazollidine-2-acetic Acid A solution of 6.49 g. (0.0151 mole) of α-triphenylmethylamino-5,5-dimethyl-3-thiazoline-2-acetic acid and 33 ml. of dimethyl phosphite was heated at 50° C. for 3 days. After cooling to room temperature, the reaction solution was taken up in 300 ml. of ethyl acetate and washed four times with 700 ml. portions of water. The organic phase was dried over anhydrous sodium sulfate, filtered, and evaporated under reduced pressure to furnish the crude product as a foam; yield 7.2 g (88%); ¹H-nmr (CDCl$_3$) ppm (δ):1.40 (s,3,CH$_3$), 1.48 (s,3,CH$_3$), 3.0 (d,J=17,1,C-3)*, 3.64 (d,J=11.2,6,OCH$_3$), others.

*penam numbering

When the above procedure is carried out at 80° C. for 6 hours the title compound is similarly obtained.

The title compound is also obtained when the above reactants dissolved in 50 ml. of chloroform are maintained at 25° C. for ten days, after which the reaction mixture was washed with water and the product isolated as described.

EXAMPLE 6

6-Triphenylmethylamino-2,2-dimethyl-3-(O,O-dimethylphosphono)penam

A. To an ice-bath cooled, stirred solution of 7.2 g. (0.0133 mole) of crude α-triphenylmethylamino-5,5-dimethyl-4-(O,O-dimethylphosphono)thiazolidine2-acetic acid and 95 ml. of dichloromethane, a solution of 1.68 g. (0.0133 mole) of 1,3-diisopropylcarbodiimide in 10 ml. of dichloromethane was added dropwise over a period of 10 minutes. The resulting solution was allowed to stand at room temperature for two days; the volatile components were then evaporated under reduced pressure, and 20 ml. of diethyl ether was added to the residue. The resulting colorless precipitate was filtered and washed with 5 ml. of diethyl ether. The combined filtrates were evaporated to afford 7.3 g. of a foam which was then submitted to chromatography on a column containing 220 g. of silica gel. Upon elution of the column with a 1:1 mixture of dichloromethane-chloroform, the title compound was obtained after some initial undesired material was discarded; yield 5.4 g. (crude); IR (KBr) cm$^{-1}$: 1022, 1063, 1183, (P-O-C); 1250 (P=O); 1785 (β-lactam); others. ¹H-nmr (CDCl$_3$) ppm (δ): 1.57 (s,3,α-CH$_3$), 1.60 (s,3β-CH$_3$), 3.08 (d,1,NH), 3.74 (d,J = 11,3,OCH$_3$), 3.77 (d,J = 11,3,OCH$_3$), 3.89 (d,J = 11,2,1,C-3), 4.47 (m,2,C-5 and C-6), 7.17–7.63 (m,15,C$_6$H$_5$).

B. When the above reaction is carried out at 0° C. for 120 hours, the title compound is likewise obtained.

C. When the procedure of Example 6A is repeated but using toluene as solvent in place of dichloromethane and carrying out the reaction at 80° C., the title compound is also obtained.

D. When the procedure of Example 6A is modified by using either 1,3-dicyclohexylcarbodiimide or 1-(3-dimethylaminopropyl)-3-ethylcarbodiimide in place of 1,3-diisopropylcarbodiimide, 6-triphenylmethylamino-2,2-dimethyl-3-(O,O-dimethylphosphono)penam is likewise obtained.

EXAMPLE 7

6-Triphenylmethylamino-2,2-dimethyl-3-(O-methylphosphono)penam

A solution of 823 mg. (1.58 millimoles)6-triphenylmethylamino-2,2-dimethyl-3-(O,O-dimethylphosphono)penam in 7 ml. of dry pyridine was stirred under a stream of nitrogen for about five minutes, then 845 mg. (6.3 millimoles) of anhydrous lithium iodide was added and the mixture heated at 40° C. for 45 minutes. An equal volume of chloroform was added and the mixture was evaporated to dryness in vacuo. The residue was taken up in ethyl acetate and evaporated again to dryness. The residue was then taken up in water, adjusted to pH 9.0 and extracted with ethyl ether. The aqueous phase was adjusted to pH 2.5 and extracted with a 3:1 mixture of ethyl acetate/ethyl ether. The extracts were backwashed with water, dried over anhydrous sodium sulfate and evaporated to dryness to obtain 293 mg. of the title compound as a colorless solid. $^1$H-nmr (CDCl$_3$) ppm ($\delta$): 1.42 (s,3,CH$_3$), 1.47 (s,3,CH$_3$), 3.57 (d,J = 11,3OCH$_3$), 3.73 (d,J = 12, 1, C-3), 4.18 (d,1,J = 4, C-5), 4.32 (m,1,C-6), 7.12–7.70 (m,15,C$_6$H$_5$-). IR(film, on pyridine salt): 1770 cm$^{-1}$ ($\beta$-lactam).

When the above process is repeated but the reaction is carried out at −30° C for 48 hours or at 100° C. for 15 minutes the title compound is similarly obtained.

EXAMPLE 8

6-Amino-2,2-dimethyl-3-(O-methylphosphono)penam p-toluenesulfonate

To a stirred slurry of 4.72 g. (0.010 mole) 6-triphenylmethylamino2,2-dimethyl-3-(O-methylphosphono)penam in 50 ml. of dry acetone was added 1.90 g. (0.010 mole) of p-toluenesulfonic acid monohydrate at ambient temperature. The solids dissolved slowly to afford a clear solution. After stirring for about 15 minutes the product started to precipitate. After stirring for about one hour the product was removed by filtration and washed with acetone. $^1$H-nmr (DMSO-d$_6$) ppm ($\delta$): 1.62 (s,3,CH$_3$), 1.70 (s,3,CH$_3$), 3.62 (d,J = 11,3,OCH$_3$), 3.88 (d,J = 11,1,C-3), 5.05 (m,1,C-6), 5.37 (d,J = 4,1,C-5). IR (Nujol mull): 1765 cm$^{-1}$($\beta$-lactam).

EXAMPLE 9

6-Amino-2,2-dimethyl-3-(O-methylphosphono)penam

Two grams of the p-toluenesulfonate salt prepared by the above procedure is dissolved in 10 ml of water. The pH is then adjusted to 3.5 and the resulting solution concentrated in vacuo to about 5 ml. The title compound is isolated to Sephadex LH-20 chromatography, eluting with water.

Sephadex LH-20 is a product of Pharmacia Fine Chemicals Co. It is a crosslinked dextran gel which separates molecules according to their size and shape; see B. Gelotte and J. Porath in "Chromatography", E. Heftmann, Ed., Reinhold Publishing Co., New York, N.Y., 1967, p. 343.

EXAMPLE 10

6-(2-Phenylacetamido)-2,2-dimethyl-3-(O-methylphosphono)penam

A stirred slurry of 532 mg. (0.002 mole) of 6-amino-2,2-dimethyl-3-(O-methylphosphono)penam in 10 ml. of water is cooled to 0° C., and the pH is then adjusted to 8.0 using 1N sodium hydroxide. To this solution is then added 0.27 ml. (310 mg., 0.002 mole) of phenylacetyl chloride, in portions, with the pH of the solution being maintained between 7 and 8 during the addition, using 0.1 N sodium hydroxide. The solution is stirred in additional 30 minutes at 0° C. and pH 7. It is concentrated in vacuo to a small volume and the title compound purified by Sephadex LH-20 chromatography, eluting with water.

EXAMPLE 11

By means of procedures analogous to that described in Example 10, but employing the appropriate acid chloride in place of phenylacetyl chloride in each case, the following compounds of formula (Ia) are similarly obtained.

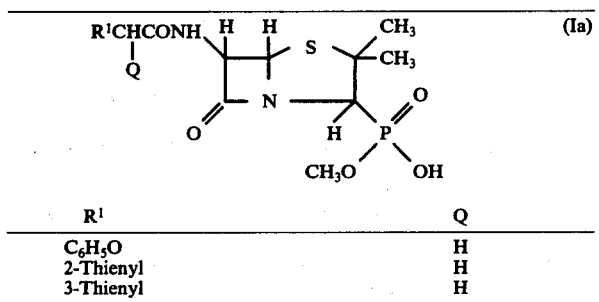

| R$^1$ | Q |
| --- | --- |
| C$_6$H$_5$O | H |
| 2-Thienyl | H |
| 3-Thienyl | H |

EXAMPLE 12

6-(D-2-Azido-2-phenylacetamido)-2,2-dimethyl-3-(O-methylphosphono)penam

A solution of 1.77 g. (0.01 mole) of D-2-azido-2-phenylacetic acid (prepared by the method of U.S. Pat. No. 3,772,364) and 5 ml. of thionyl chloride is heated under reflux for an hour. The reaction solution is evaporated under reduced pressure to furnish a residue of D-2-azido-2-phenylacetyl chloride which is then dissolved in 10 ml. of dichloromethane and is added over 5 minutes to a stirred, ice-bath cooled solution of 2.66 g. (0.01 mole) of 6-amino-2,2-dimethyl-3-(O-methylphosphono)penam, 2.02 g. (0.02 mole) of triethylamine and 50 ml. of dichloromethane. After 30 minutes the reaction solution is allowed to warm to room temperature. After a further 3 hours, the more volatile components of the solution are evaporated under reduced pressure and the residue is taken up in 50 ml. of water. The aqueous solution is washed twice with 25 ml. portions of ethyl acetate, and it is then adjusted to pH 2.5 by the careful addition of 6 N hydrochloric acid. The resulting cloudy mixture is extracted twice with 30 ml. portions of ethyl acetate. After being dried over anhydrous sodium sulfate, the combined extracts are filtered and the solvent is evaporated under reduced pressure to obtain the title compound.

EXAMPLE 13

6-(D-2-amino-2-phenylacetamido)-2,2-dimethyl-3-(O-methylphosphono)penam

The title compound is prepared from 6-(D-2-azido-2-phenylacetamido)-2,2-dimethyl-3-(O-methylphosphono)penam by catalytic hydrogenation procedures analogous to those described by Ekstrom, et al., Acta Chemica Scandinavica, 19, 281 (1965); see also U.S. Pat. No. 3,385,847.

EXAMPLE 14

6-(D-2-amino-2-phenylacetamido)-2,2-dimethyl-3-(O-methylphosphono)penam

A stirred suspension of 266 mg. (0.001 mole) of 6-amino-2,2-dimethyl-3-(O-methylphosphono)penam in 5 ml. of water is cooled to 0°-5° C. in an ice-bath. The pH is then adjusted to 7.0 using a dilute sodium hydroxide solution. At this point 310 mg. (0.0015 mole) of D-2-amino-2-phenylacetyl chloride hydrochloride (Hardcastle et al., *Journal of Organic Chemistry*, 31, 897 (1966)) is added portionwise during 15 minutes at 0°-5° C., and with the pH maintained between 6 and 7 by the addition of dilute sodium hydroxide. At the end of the addition, the reaction mixture is stirred for a further 15 minutes and then filtered. The pH of the filtrate is adjusted to 4.4 with dilute hydrochloric acid, and and solution is stored overnight in the refrigerator. The mixture is then filtered, and the filtrate is placed on a column of 25 g. of Sephadex LH-20 (Pharmacia Fine Chemicals, Inc.) made up in water. The column is eluted with water, taking fractions, and the composition of each fraction is assayed by thin-layer chromatography. The fractions containing the pure product are combined and evaporated under high vacuum to a volume of approximately 1 ml. After this solution has set for a few days, 6-(D-2-amino-2-phenylacetamido)-2,2-dimethyl-3-(O-methylphosphono)penam crystallizes. It is filtered, washed briefly with water and is dried.

EXAMPLE 15

6-(D-2-Amino-2-phenylacetamido)-2,2-dimethyl-3-(O-methylphosphono)penam

To a stirred solution of 2.38 ml (2.71 g., 0.025 mole) of ethyl chloroformate in 60 ml. of acetone, is added 2.5 ml. of a 3% solution of N-methylmorpholine in acetone. The resulting solution is cooled to −40° C., and then 7.52 g. (0.028 mole) of sodium D-2-(1-methoxycarbonyl-1-propen-2-ylamino)-2-phenylacetate is added. The temperature is adjusted to −20° C. and stirring is continued for 30 minutes. The solution is recooled to −40° C., and an ice-cold solution, prepared by suspending 6.65 g. (0.025 mole) of 6-amino-2,2-dimethyl-3-(O-methylphosphono)penam in 25 ml. of water and then adjusting the pH to 7.0, is added. The resulting solution is stirred for 30 minutes without further cooling, and then the acetone is removed by evaporation under reduced pressure. To the aqueous residue is added an equal volume of tetrahydrofuran, and then, at 5° C. the pH is adjusted to 1.5 with dilute hydrochloric acid. The mixture is held at this temperature and pH for 30 minutes, and then the tetrahydrofuran is removed by evaporation under reduced pressure. The aqueous residue is washed once with ethyl acetate and once by ether; the washes are discarded. The pH of the remaining aqueous phase is raised to 4.5, and the product isolated by Sephadex LH-20 chromatography. The sodium D-2-(1-methoxycarbonyl-1-propen-2-ylamino)-2-phenylacetate is prepared from methyl acetoacetate and D-2-amino-2-phenylacetic acid by a procedure analogous to that used by Long et at. [*Journal of the Chemical Society* (London), Part C, 1920 (1971)]for the preparation of the corresponding p-hydroxy-phenyl compound.

When the above procedure is repeated, but using an equimolar amount of sodium D-2-(1-ethoxycarbonylpropen-2-ylamino)-2-phenylacetate in place of Sodium D-(1-methoxycarbonyl-1-propen-2-ylamino)-2-phenylacetate, the results are substantially unchanged.

EXAMPLE 16

6-[D-2-Amino-2-(4-hydroxyphenyl)acetamido]-2,2-dimethyl-3-(O-methylphosphono)-penam To a stirred solution of 0.19 ml. (217 mg., 0.002 mole) of ethyl chloroformate in 15 ml. of dry acetone, cooled to 0° C., is added one drop of N-methylmorpholine, and 576 mg. (0.002 mole) of sodium D-2-(1-methoxycarbonyl1-propen-2-yl-amino)-2-(4-hydroxyphenyl)acetate [Long et al. *Journal of the Chemical Society* (London), Part C, 1920 (1971)]. The mixture is stirred for a further 30 minutes and is then cooled to about −35° C. To it is then added an ice-cold solution of the sodium salt of 6-amino-2,2-dimethyl-3-(O-methylphosphono)penam, prepared by adding 10% aqueous sodium hydroxide to a suspension of 532 mg. (0.002 mole) of 6-amino-2,2-dimethyl-3-(O-methylphosphono)penam in 5 ml. of water (to give a pH of 7.8), then diluting with 25 ml. of acetone. The cooling bath is removed, and the reaction mixture is stirred for a further 30 minutes. At this point, the acetone is removed by evaporation under reduced pressure, and then 20 ml. of methyl isobutyl ketone is added to the remaining aqueous solution. The two-phase system is cooled to 10° C., is adjusted to pH 0.9 with dilute hydrochloric acid, and then is stirred at 10° C. for one hour. The methyl isobutyl ketone phase is separated and discarded. The aqueous phase is adjusted to pH 4.5, and is then stored in a refrigerator for 3 hours. The precipitate which forms is filtered, giving 6-[D-2-amino2-(4-hydroxyphenyl)acetamido]-2,2-dimethyl-3-(O-methylphosphono)penam. It can be further purified by Sephadex LH-20 chromatography.

EXAMPLE 17

6-[D-2-Amino-2-(3-thienyl)acetamido]-2,2-dimethyl-3-(O-methylphosphono)penam The procedure of Example 16 is repeated, except that the sodium D-2-(1-methoxycarbonyl-1-propen-2-ylamino)-2-(4-hydroxyphenyl)acetate used therein is replaced by an equal molar amount of sodium D-2-(1-methoxycarbonyl-1-propen-2-ylamino)-2-(3-thienyl)acetate. There is obtained 6-[D-2-amino-2-(3-thienyl)acetamido]-2,2-dimethyl-3-(O-methylphosphono)penam.

The sodium D-2-(1-methoxycarbonyl-1-propen-2-ylamino)-2-(3-thienyl)-acetate used in this example is prepared from D-2-(3-thienyl)glycine and methyl acetoacetate using a method analogous to that described by Long et al. [*Journal of the Chemical Society* (London), Part C, 1920 (1971)] for the condensation of D-2-(4-hydroxyphenyl)glycine with methyl acetoacetate. The D-2-(3-thienyl)glycine is prepared from thiophene-3-carboxaldehyde by a Strecker reaction, followed by resolution of the racemic 2-(3-thienyl)glycine so produced into its optical antipodes [Nishimura et al., Nippon Kagaku Zasshi, 82, 1688 (1961); Chemical Abstracts, 58, 11464 (1963)].

EXAMPLE 18

6-[D-2-Amino-2-(1,4-cyclohexadienyl)acetamido]-2,2-dimethyl-3-(O-methylphosphono)penam At 0° C., a stirred suspension of 532 mg. (0.002 mole) of 6-amino-2,2-dimethyl-3-(O-methylphosphono)penam in 35 ml. of water is adjusted to pH 7.0 by the monitored addition of 1.0 N aqueous sodium hydroxide. When all the solid has dissolved, the solution is adjusted to pH 6.0 by the addition of 1.0 N hydrochloric acid, and 500 mg. (0.028 mole) of D-4-(1,4-cyclohexadienyl)-1,3-oxazolidin-2,5-dione is then added. The reaction mixture is stirred at about 0° C. and at pH 6.0 for one hour. It is then filtered. The filtrate is adjusted to pH 4.2, and is then lyophilized. The residue is dissolved in 5 ml. of dichloromethane containing 0.55 ml. (400 mg., 0.004 mole) of triethylamine. This new solution is added dropwise with stirring to 100 ml. of diethyl ether, and the solid which precipitates is filtered to afford the title compound as its triethylamine salt.

D-4-(1,4-Cyclohexadienyl)-1,3-oxazolidin-2,5-dione is prepared from 2.0 g. (0.0131 mole) of D-2-(1,4-cyclohexadienyl)glycine [Dolfini et al., *Journal of Medicinal Chemistry*, 14, 117 (1971)] and phosgene using methods analogous to those described by Alburn et al., *Antimicrobial Agents and Chemotherapy*, 586 (1967): yield 1.2 g. (51%).

EXAMPLE 19

6-(2-[2-(Aminomethyl)phenyl]acetamido)-2,2-dimethyl-3-(O-methylphosphono)penam

To a stirred solution of 2.85 g. (0.01 mole) of sodium 2-(1-methoxycarbonyl-1-propen-2-ylaminomethyl)phenylacetate (U.S. 3,813,376) in 35 ml. of tetrahydrofuran under a nitrogen atmosphere and cooled to −15° C. is added first 3 drops of N-methylmorpholine, and then 0.95 ml. (1.08 g., 0.01 mole) of ethyl chloroformate. After stirring for 30 minutes at −15° C., the reaction mixture is treated with a solution of 2.66 g. (0.01 mole) of 6-amino-2,2-dimethyl-3-(O-methylphosphono)penam, 20 ml. of tetrahydrofuran and 10 ml. of water adjusted to pH 7.4 by the monitored addition of 1N aqueous sodium hydroxide. The resulting mixture is allowed to stir at room temperature for 30 minutes, and the tetrahydrofuran is subsequently evaporated under reduced pressure.

The residual aqueous solution at 0° C. is adjusted to pH 1.5 using 3N hydrochloric acid, and is stirred for 30 minutes. The solution is rapidly washed with 40 ml. of ethyl acetate, the aqueous layer is separated, adjusted to pH 5 and concentrated. The concentrate is stored overnight at approximately 10° C. The first crop of the product is filtered, and the filtrate is concentrated under reduced pressure to approximately half-volume. Cooling results in the formation of additional precipitate, which is filtered, combined with the first crop and dried to afford the title compound. The product can be further purified by Sephadex LH-20 chromatography.

EXAMPLE 20

6-(2-[2-(Azidomethyl)phenyl]acetamido)-2,2-dimethyl-3-(O-methylphosphono)penam

The procedure of Example 12 is repeated except that D-2-azido-2-phenylacetic acid used therein is replaced by an equimolar amount of 2-(azidomethyl)phenylacetic acid (U.S. Pat. No. 3,813,376), whereupon the title compound is obtained.

EXAMPLE 21

6-(2-[2-(Aminomethyl)phenyl]acetamido)-2,2-dimethyl-3-(O-methylphosphono)penam

When the procedure of Example 13 is repeated except that 6-D-(2-azido-2-phenylacetamido)-2,2-dimethyl-3-(O-methylphosphono)penam is replaced by an equimolar amount of 6-(2-[2-(azidomethyl)phenyl]acetamido)-2,2-dimethyl-3-(O-methylphosphono)penam, the title compound is obtained.

EXAMPLE 22

6-(2-Carboxy-2-phenylacetamido)-2,2-dimethyl-3-(O-methylphosphono)penam

To a stirred solution of 266 mg. (0.001 mole ) of 6-amino-2,2-dimethyl-3-(O-methylphosphono)penam in 8 ml. of water is added dropwise dilute aqueous sodium hydroxide to obtain a pH of 6.1. To this solution is then added 235 mg. (0.0013 mole) of phenylmalonic acid, followed by 190 mg. (0.001 mole) of 1-ethyl-3-(3-dimethylaminoprop-1-yl)carbodiimide hydrochloride. The solution is stirred for 3.5 hours, during which time the pH is maintained in the range from 6.1 to 6.3 by the dropwise addition of dilute hydrochloric acid. At this point, the pH is raised to 7.3 by the addition of saturated sodium hydrogen carbonate solution, and the reaction mixture is washed with ethyl acetate. The wash is discarded. The aqueous phase is then adjusted to pH 2 using dilute hydrochloric acid, and then it is extracted twice with 30 ml. portions of ethyl acetate. The combined extracts are dried, and concentrated to a volume of about 25 ml. To this solution is added a solution of 330 mg. (0.002 mole) of sodium 2-ethylhexanoate in 2.0 ml. of ethyl acetate. The precipitate which forms is filtered to give the disodium salt of 6-(2-carboxy-2-phenylacetamido)-2,2-dimethyl-3-(O-methylphosphono)penam.

EXAMPLE 23

6-[2-Carboxy-2-(2-thienyl)acetamido]-2,2-dimethyl-3-(O-methylphosphono)penam

To a stirred suspension of 370 mg. (0.002 mole) of 2-(2-thienyl)-malonic acid (Netherlands Patent No. 6805524) in 4 ml. of water is added 532 mg. (0.002 mole) of 6-amino-2,2-dimethyl-3-(O-methylphosphono)penam. The pH is then adjusted to 6.5 using 20% aqueous sodium hydroxide. The resulting solution is cooled to 0° C. and 384 mg. (0.002 mole) of 1-ethyl-3-(3-dimethylaminoprop-1-yl)carbodiimide hydrochloride is added. The solution is stirred for 3.5 hours at 0° C., with the pH maintained between 6 and 7 using 1N hydrochloric acid. At this point, the pH of the solution is then lowered to 2.0 and the mixture is extracted with two 30 ml. portions of ethyl acetate. The combined extracts are dried, and are then concentrated to about 15 ml. To this solution is added a solution of 665 mg. (0.004 mole) of sodium 2-ethylhexanoate in 2.6 ml. of ethyl acetate. The solid which precipitates is filtered, and dried to give 6-[2-carboxy-2-(2-thienyl)acetamido]-2,2-dimethyl-3-(O-methylphosphono)penam as its disodium salt.

EXAMPLE 24

6-[2-Carboxy-2-(3-thienyl)acetamido]-2,2-dimethyl-3-(O-methylphosphono)penam

The reaction of 370 mg. (0.002 mole) of 2-(3-thienyl)-malonic acid (British Patent No. 1.125,557) with 532 mg. (0.002 mole) of 6-amino-2,2-dimethyl-3-(O-methylphosphono)penam according to the procedure of Example 23 affords the title compound as its disodium salt.

EXAMPLE 25

6-(2-Sulfo-2-phenylacetamido)-2,2-dimethyl-3-(O-methylphosphono)penam

To a stirred slurry of 266 mg. (0.001 mole) of 6-amino-2,2-dimethyl-3-(O-methylphosphono)penam in 5 ml. of methylene chloride is added 0.25 ml. of triethylamine. This is stirred for 45 minutes, and is then cooled to about 0° C. To this is then added a solution, in 6 ml. of methylene chloride, of 389 mg. (0.001 mole) of the mixed carbonic-carboxylic anhydride formed by reacting the bis-triethylamine salt of 2-sulfo-2-phenylacetate acid with one equivalent of ethyl chloroformate [Nicolaus, et al., Annali di Chimica (Rome), 53, 14 (1963)]. The reaction mixture is then stirred at 0° C. for a further 1.5 hours after the addition of the anhydride. At this point the reaction mixture is filtered, and a solution of 330 mg. (0.002 mole) of sodium 2-ethylhexanoate in ethyl acetate is added. The precipitate which forms is filtered, giving the crude product as its disodium salt. The crude product is purified by dissolving it in water and adding the solution to a column of 25 g. of Sephadex LH-20 (Pharmacia Fine Chemicals, Inc.) made up in water. The column is eluted with water, taking fractions, and the composition of the fractions is assayed by thin-layer chromatography. The fractions containing the pure product are combined and lyophilized, giving the disodium salt of the title compound.

EXAMPLE 26

6-Amino-2,2-dimethyl-3-(O,O-dimethylphosphono)penam

A. To a stirred slurry of 6-triphenylmethylamino-2,2-dimethyl-3-(O,O-dimethylphosphono)penam, 487 mg. (0.001 mole), in 10 ml. of dry acetone is added 190 mg. (0.001 mole) of p-toluenesulfonic acid monohydrate at 25° C. The solids dissolve slowly, giving a clear solution. After stirring at 25° C. for 15 minutes the product starts to precipitate. The stirring is continued for a further 45 minutes after the product starts to appear. The first crop is then filtered off, washed with acetone, and dried to afford the title compound as the p-toluenesulfonate salt. $^1$H-nmr (DMSO-d$_6$) ppm ($\delta$): 1.65 (s,3,CH$_3$), 1.70 (s,3,CH$_3$), 2.32 (s,3,CH$_3$), 3.77 (d,J = 11,6,OCH$_3$), 4.11 (d,J = 11, 1,C-3), 5.1 (m,l)- and 5.45 (d,J = 4,1)-C-5 and C-6 protons, 7.3 (q,4,aromatic protons). The yield is 83% of theory, M.P. 149°-151° C.

B. To a solution of 300 mg. of the above p-toluenesulfonate salt in 10 ml. of dichloromethane is added 67 mg. of triethylamine. The solution is stirred vigorously for a few minutes, after which the organic layer is separated, diluted with ether and filtered. The filtrate is dried over anhydrous magnesium sulfate and evaporated to dryness in vacuo. The residue is 6-amino-2,2-dimethyl-3-(O,O-dimethylphosphono)penam.

EXAMPLE 27

6-(2-Phenylacetamido)-2,2-dimethyl-3-(O,O-dimethylphosphono)penam

To a solution of 338 mg. (0.75 millimole) of the p-toluenesulfonate salt of 6-amino-2,2-dimethyl-3-(O,O-dimethylphosphono)penam in 10 ml. of chloroform was added an equal volume of water. The pH was adjusted to 7.5 and after thorough mixing the layers were separated. The organic layer was dried over sodium sulfate and concentrated to a dry foam to obtain 163 mg. (78%) of the free base.

The free base was dissolved in 5 ml. of dichloromethane, the solution cooled in an ice/methanol bath and 0.1 ml. of triethylamine followed by the dropwise addition of a solution of 90 mg. (0.58 millimole) of phenylacetyl chloride in 5 ml. of solvent. The mixture was stirred for 10 minutes after the addition was completed, the cooling bath removed and stirring continued for 20 minutes. The reaction mixture was then washed successively with water, water adjusted to pH 3.0, and saturated brine solution. The organic layer was dried over anhydrous sodium sulfate and concentrated to dryness to obtain 200 mg. of the title compound as a solid foam. $^1$H-nmr(CDCl$_3$) ppm ($\delta$): 1.53 (s,3,CH$_3$), 1.73 (s,3,CH$_3$), 3.60 (s,2,—CH$_2$—), 3.83 (d,J=11,6,OCH$_3$), 3.88 (d, J=11.5,1,C-3), 5.35 (d,J=4,1,C-5), 5.65 (m,1,C-6), 7.32 (s,5,C$_6$H$_5$-). IR (film) cm$^{-1}$: 1785 ($\beta$-lactam), 1665 (amide), 1240 (—P=O), 1040 (POCH$_3$).

EXAMPLE 28

6-(2-Phenoxyacetamido)-2,2-dimethyl-3-(O,O-dimethylphosphono)penam

To a solution of 0.681 g. (1.5 millimoles) of 6-amino-2,2-dimethyl-3-(O,O-dimethylphosphono)penam p-toluenesulfonate salt in 50 ml. of dichloromethane at 0° C. was added 0.44 ml. (4millimoles) of N-methylmorpholine. To this solution was added dropwise over ten minutes a solution of 0.21 ml. (1.5 millimole) of phenoxyacetyl chloride in 10 ml. of solvent. The mixture was then stirred for two hours, washed with water at pH 6.6, water at pH 3.0 and finally with water at pH 8.5. The organic layer was dried over anhydrous sodium sulfate and evaporated to dryness to obtain 0.65 g. of the title compound as a tan powder. $^1$H-nmr (CDCl$_3$) ppm ($\delta$): 1.67 (s,3,CH$_3$), 1.80 (s,3,CH$_3$), 3.87 (d,J=11,6OCH$_3$), 3.97 (d,J=12,1,C-3), 4.55 (s,2,—CH$_2$—), 5.43 (d,J=4,1,C-5), 5.78 (m,1,C-6), 7.13 (m,5,C$_6$H$_5$).

EXAMPLE 29

6-(D-2-Amino-2-phenylacetamido)-2,2-dimethyl-3-(O,O-dimethylphosphono)penam

When the procedure of Example 15 was repeated but employing 6-amino-2,2-dimethyl-3-(O,O-dimethylphosphono)penam in place of the corresponding-3-(O-methylphosphono)penam, the title compound was obtained in 65% yield. $^1$H-nmr (CDCl$_3$) ppm ($\delta$): 1.67 (s,3,CH$_3$), 1.80 (s,3,CH$_3$), 3.85 (d,J=10.5,6,OCH$_3$), 3.97 (d,J=12,1,C-3), 4.58 (s,1,C$\underline{H}$-NH$_2$), 5.41 (d,J=4,1,C-5), 5.68 (m,1,C-6), 7.38 (s,5,C$_6$H$_5$). IR (film) cm$^{-1}$: 1785 ($\beta$-lactam), 1235 (P=O), 1035 (P-OCH$_3$).

EXAMPLE 30

When 6-amino-2,2-dimethyl-3-(O,O-dimethylphosphono)penam is acylated by suitable modification of the procedures indicated in the table below, the following compounds of formula (Ia) are obtained.

| R$^1$ | Q | Procedure of Example No. |
|---|---|---|
| C$_6$H$_5$— | NH$_2$ | 12 plus 13, 14 |
| 4-HOC$_6$H$_4$— | NH$_2$ | 16 |
| 1,4-Cyclohexadienyl | NH$_2$ | 18 |

-continued

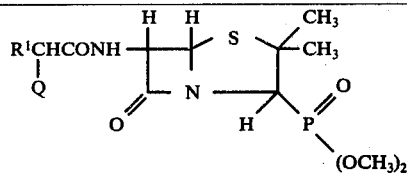

| R¹ | Q | Procedure of Example No. |
|---|---|---|
| 3-Thienyl | NH₂ | 17 |
| 2-(NH₂CH₂)C₆H₄— | H | 19, 20 plus 21 |
| 2-Thienyl | H | 10, 12, 27 |
| 3-Thienyl | H | 10, 12, 27 |
| C₆H₅— | COOH | 22 |
| 2-Thienyl | COOH | 23 |
| 3-Thienyl | COOH | 24 |
| C₆H₅— | SO₃H | 25 |

EXAMPLE 31

6-Amino-2,2-dimethyl-3-(O-methylphosphono)penam

To a solution of 535 mg. (0.004 mole) of anhydrous lithium iodide in 20 ml. of dry pyridine is added 452 mg. (0.001 mole) of 6-amino-2,2-dimethyl-3(O,O-dimethylphosphono)penam p-toluenesulfonate. The resulting mixture is stirred at 40° C. for 45 minutes then the pyridine was removed by evaporation at reduced pressure. The residue is distributed between 25 ml. each of water and ethyl ether. The ether layer is discarded and the aqueous layer extracted again with ether. The aqueous layer was then adjusted to pH 3.5 and concentrated. The title compound frequently crystallizes from the concentrated solution or can be purified by chromatography on Sephadex LH-20, eluting with water.

EXAMPLE 32

6-(2-Phenylacetamido)-2,2-dimethyl-3-(O-methylphosphono)penam, Sodium Salt 6-(2-Phenylacetamido)-2,2-dimethyl-3-(O,O-dimethylphosphono)penam (171 mg., 0.43 millimole) was dissolved in 2 ml. of dry pyridine and anhydrous lithium iodide (230 mg., 1.72 millimoles) added. The resulting mixture was stirred at room temperature for 4 hours, the pyridine evaporated under reduced pressure and 3 ml. of ethyl acetate added. The mixture was stirred, then evaporated to dryness a second time. The residue was distributed between water at pH 8.0 and ethyl ether. The aqueous phase was washed again with ether then adjusted to pH 2.8 and extracted three times with ethyl acetate. The extracts were discarded and the aqueous phase adjusted to pH 6.5 by addition of dilute sodium hydroxide solution. The title compound was obtained by lyophilization. ¹H-nmr of sodium salt (D₂O) ppm (δ): 1.57 (s,3CH₃), 1.73 (s,3, CH₃), 3.70 (d, J=10.5,3,OCH₃), 3.73 (s,2,CH₂), 3.98 (d,J=12,1,C-3), 5.50 (m,2,C-5 and C-6), 7.38 (s,5C₆H₅). IR (KBr) cm⁻¹: 1770 (β-lactam), 1190 (P=O), 1035 (P-OCH₃).

EXAMPLE 33

6-(2-Phenoxyacetamido)-2,2-dimethyl-3-(O-methylphosphono)penam, sodium salt 6-(2-Phenoxyacetamido)-2,2-dimethyl-3-(O,O-dimethylphosphono)penam (0.65 g., 1.57 millimoles), 6 ml. of pyridine and lithium iodide (0.84 g., 6.29 millimoles) were reacted according to the procedure of Example 32. The resulting -3-(O-methylphosphono)penam was converted to the sodium salt by treatment with an ethyl acetate solution of the acid with sodium 2-ethylhexanoate (Yield 45%). ¹H-nmr (D₂O) ppm (δ): 1.55 (s,3, CH₃), 1.80 (s,3,CH₃), 3.73 (d,J=10,3,OCH₃), 3.97 (d,J=11,1,C-3), 4.48 (s,2,CH₂), 5.57 (m,2,C-5 and C-6), 6.93 (m,5,C₆H₅).

EXAMPLE 34

6-(2-Amino-2-phenylacetamido)-2,2-dimethyl 3-(O-methylphosphono)penam

To a solution of 300 mg. (0.726 millimole) of 6-(2-amino-2-phenylacetamido)-2,2-dimethyl-3-(O,O-dimethylphosphono)penam in 2.8 ml. of dry pyridine was added 388 mg. (2.9 millimoles) of anhydrous lithium iodide. The resulting mixture was stirred at room temperature overnight. The pyridine was evaporated in vacuo at about 35° C. Two 5 ml. portions of chloroform were added and stripped to effect removal of the last traces of pyridine. The residue was stirred with 5 ml. of water adjusted to pH 3.0 and extracted three times with 10 ml. portions of chloroform while maintaining the aqueous phase at pH 3.0. The aqueous layer was then adjusted to pH 6.0 and dialyzed for 20 minutes, changing the water at 5 minute intervals. The dialyzed aqueous layer was adjusted to pH 6.5, lyophilized and finally dried over phosphorus pentoxide to obtain 0.294 g. of the title compound. A 240 mg. portion of the sample was further purified by passing it over a 20 ml. bed of SephadexLH 20, eluting with water. Fractions (10 ml. each) 3 through 6 containing the desired product were combined and lyophilized. A portion was converted to the sodium salt for nmr. ¹H-nmr (D₂O) ppm (δ): 1.37 (s,3,CH₃), 1.60 (s,3,CH₃), 3.58 (d, J=10,3,OCH₃), 3.80 (d,J=11,1,C-3), 5.07 (s,1, CHNH₂), 5.38 (m,2,C-5 and C-6), 7.43 (s,5, C₆H₅). IR (Nujol mull) cm⁻¹: 1768 (β-lactam), 1210 (P=O), 1065 (P-OCH₃).

EXAMPLE 35

6-(D-2-amino-2-phenylacetamido)-2,2-dimethyl-3-(O-methylphosphono)penam

A. 6-(D-2-azido-2-phenylacetamido)-2,2-dimethyl-3-(O,O-dimethylphosphono)penam, 439 mg. (0.001 mole), prepared by reacting D-2-azido-2-phenylacetyl chloride and 6-amino-2,2-dimethyl-3-(O,O-dimethylphosphono)penam by suitable modification of the procedure of Example 12 and 535 mg. (0.004 mole) of anhydrous lithium iodide in 25 ml. of dry pyridine is stirred at room temperature for three hours, after which the pyridine is evaporated in vacuo. The residue is dissolved in water and washed with ether to remove traces of pyridine remaining. The aqueous layer is adjusted to pH 2.5 and extracted with dichloromethane. The organic layer is dried over anhydrous sodium sulfate and evaporated to dryness in vacuo to obtain 6-(D-2-azido-2-phenylacetamido)-2,2-dimethyl-3-(O-methylphosphono)penam.

B. The product from part A is then subjected to catalytic hydrogenation as described in Example 13 to obtain the title compound.

EXAMPLE 36

6-(2-[2-(Aminomethyl)phenyl]acetamido-2,2-dimethyl-3-(O-methylphosphono)penam

When the procedure of Example 35 is repeated using 6-(2-[2-azidomethyl)phenyl]acetamido-2,2-dimethyl-3-(O,O-dimethylphosphono)penam as starting material, the title compound is obtained.

The 6-(2-[2-azidomethyl)phenyl]acetamido-2,2-dimethyl-3-(O,O-dimethylphosphono)penam is prepared by suitable modification of the procedure of Example 20 and employing 6-amino-2,2-dimethyl-3-(O,O-dimethylphosphono)-penam in place of the corresponding -3-(O-methylphosphono)penam.

EXAMPLE 37

When the procedures of Examples 32-34 are repeated but using the appropriate starting material, selected from the products of Example 30, in place of 6-amino-2,2-dimethyl-3-(O,O-dimethylphosphono)penam p-toluenesulfonate, the following compounds of formula (Ib) are obtained.

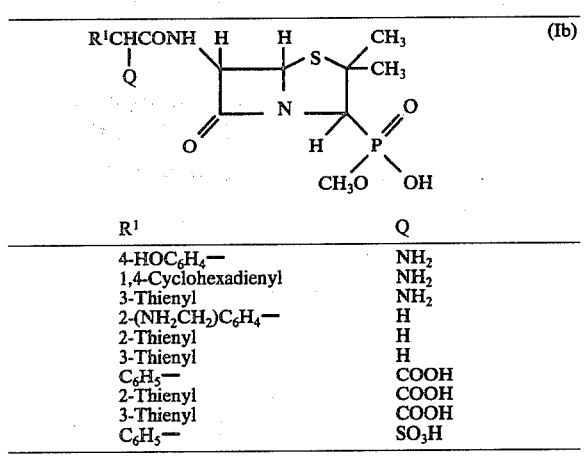

| $R^1$ | Q |
|---|---|
| 4-HOC$_6$H$_4$— | NH$_2$ |
| 1,4-Cyclohexadienyl | NH$_2$ |
| 3-Thienyl | NH$_2$ |
| 2-(NH$_2$CH$_2$)C$_6$H$_4$— | H |
| 2-Thienyl | H |
| 3-Thienyl | H |
| C$_6$H$_5$— | COOH |
| 2-Thienyl | COOH |
| 3-Thienyl | COOH |
| C$_6$H$_5$— | SO$_3$H |

EXAMPLE 38

6-(2-Phenoxyacetamido)-2,2-dimethyl-3-phosphonopenam, sodium salt 6-(2-Phenoxyacetamido)-2,2-dimethyl-3-(O,O-dimethylphosphono)penam (833 mg., 2.0 millimoles) was dissolved in 8 ml. of dry pyridine and anhydrous lithium iodide (1.07 g., 8.0 millimoles) was added. The mixture was stirred for five minutes then 1.53 ml. (12 millimoles) of trimethylchlorosilane was added and the reaction stirred under nitrogen at 45° C. for 4.25 hours. After storing overnight at −70° C. the reaction mixture was warmed to 40° C. and the pyridine evaporated in vacuo. The residue was taken up in water, adjusted to pH 8.0, and extracted three times with chloroform. The aqueous layer was then adjusted to pH 1.5 and extracted three times with ethyl acetate, the organic phase dried over sodium sulfate and added to a solution of 3 millimoles of sodium 2-ethylhexanoate in ethyl acetate. The mixture was stirred 15 minutes, then allowed to stand for 15 minutes. An oil separated which was washed twice with ethyl acetate then triturated in the same solvent to effect solid formation. The solid was filtered, washed with a mixture of ethyl acetate/ethyl ether, then dried in vacuo to obtain 0.287 g. of the title compound. IR (KBr) cm$^{-1}$: 1754 ($\beta$-lactam), 1240 (P=O).

A sample was acidified to pH 1.5, extracted with ethyl acetate, dried over anhydrous sodium sulfate and evaporated to dryness to obtain the free acid. $^1$H-nmr (CDCl$_3$) ppm ($\delta$): 1.57 (s,3,CH$_3$), 1.75 (s,3,CH$_3$), 4.08 (d,J=14,1,C-3), 4.53 (s,2,CH$_2$), 5.60 (m,2,C-5 and C-6), 7.13 (m,5,C$_6$H$_5$). IR (CHCl$_3$) cm$^{-1}$: 1778 ($\beta$-lactam).

When the above process is repeated but the reaction is carried out at −30° C. for 54 hours or at 100° C. in a pressure reactor for 20 minutes, the title compound is also obtained.

When a sample of 6-(2-phenoxyacetamido)-2,2-dimethyl-3-phosphonopenam was dissolved in ether and treated with an excess of diazomethane, 6-(2-phenoxyacetamido)-2,2-dimethyl-3-(O,O-dimethylphosphono)penam was obtained as ascertained by comparison of NMR and infrared spectra with that of an authentic sample.

EXAMPLE 39

6-(2-phenylacetamido)-2,2-dimethyl-3-phosphonopenam 6-(2-phenylacetamido)-2,2-dimethyl-3-(O-methylphosphono)penam (384 mg., 1.0 millimole) is dissolved in 4 ml. of dry pyridine then trimethylchlorosilane (0.381 ml., 3.0 millimoles) and lithium iodide (536 mg., 4.0 millimoles) are added. The reaction mixture is stirred under nitrogen at 25° C. for 5 hours after which 2 ml. of water is added. The mixture is stirred for 10 minutes then the volatiles removed by evaporation in vacuo. The residue was taken up in water, adjusted to pH 8.0 and extracted with 3 × 10 ml. of chloroform. The aqueous phase was then acidified to pH 1.5 and extracted with 3 × 10 ml. of ethyl acetate. The ethyl acetate extracts were dried over sodium sulfate then evaporated to dryness to obtain the title compound.

When the procedure is repeated but the reaction mixture is held at −30° C. for two days or at 100° C. in a sealed glass tube for 15 minutes, the title compound is obtained in a like manner.

EXAMPLE 40

Treatment of the appropriate compound of formula (XII) by the procedure of Example 38 in those cases where $R^2$ is methyl or by the procedure of Example 39 when $R^2$ is hydrogen, affords the following -3-phosphonopenams of formula (Ic)

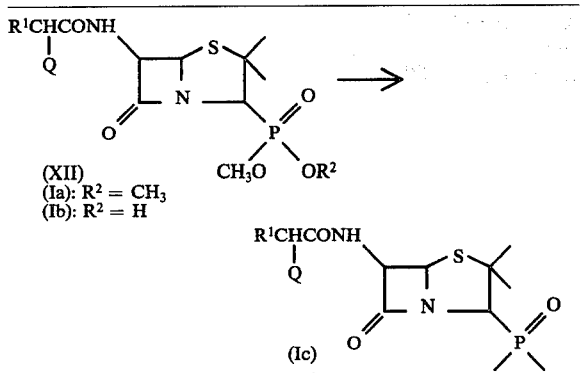

| $R^1$ | Q | $R^2$ |
|---|---|---|
| 2-Thienyl | H | H |
| 3-Thienyl | H | CH$_3$ |
| C$_6$H$_5$ | COOH | CH$_3$ |
| C$_6$H$_5$ | COOH | H |
| 2-Thienyl | COOH | CH$_3$ |
| 3-Thienyl | COOH | CH$_3$ |
| C$_6$H$_5$ | SO$_3$H | CH$_3$ |
| C$_6$H$_5$ | NH$_2$ | CH$_3$ |
| 4-HOC$_6$H$_4$ | NH$_2$ | CH$_3$ |
| 1,4-Cyclohexadienyl | NH$_2$ | H |
| 3-Thienyl | NH$_2$ | CH$_3$ |
| 2-(NH$_2$CH$_2$)C$_6$H$_4$— | H | H |

EXAMPLE 41

6-(D-2-Amino-2-phenylacetamido)-2,2-dimethyl-3-(O-methylphosphono)penam Hydrochloride A slurry of 100 mg. of 6-(D-2-amino-2-phenylacetamido)-2,2-dimethyl-3-(O-methylphosphono)penam in 4 ml. of deionized water is stirred for 5 minutes at room temperature. The pH is adjusted to 2.0 using dilute hydrochloric acid and the resulting solution is immediately lyophilized to afford the title compound.

EXAMPLE 42

6-(D-2-Amino-2-[4-hydroxyphenyl]acetamido)-2,2-dimethyl-3-(O-methylphosphono)penam, Potassium Salt To a stirred solution of 2.0 g. of 6-(D-2-amino-2-[4-hydroxyphenyl]-acetamido-2,2-dimethyl-3-(O-methylphosphono)penam in 100 ml. of methanol, cooled to −30° C. is added dropwise 5.0 ml. of 1.0N potassium hydroxide solution in methanol. The mixture is allowed to warm to 0° C., and then it is added dropwise with stirring to 700 ml. of ether. The precipitate is collected by filtration and dried under high vacuum to afford the title potassium salt.

When the above procedure is repeated, except that the potassium hydroxide used therein is replaced by an equimolar amount of sodium hydroxide, the product is the sodium salt of 6-D-2-amino-2-[4-hydroxyphenyl]-acetamido)-2,2-dimethyl-3-(O-methylphosphono)penam.

EXAMPLE 43

6-(D-2-Amino-2-[4-hydroxyphenyl]acetamido)-2,2-dimethyl-3-(O-methylphosphono)penam, Calcium Salt To a stirred solution of 4.0 g. of 6-(D-2-amino-2-[4-hydroxyphenyl]-acetamido-2,2-dimethyl-3-(O-methylphosphono)penam in 40 ml. of dimethylformamide is added a turbid solution of 0.37 g. of calcium hydroxide over 5 minutes. The mixture is heated at 35°–40° C. for 1 hour, and then an additional 50 ml. of dimethylformamide is added. Heating at 35°–40° C. is continued for a further 30 minutes, after which the solution is added dropwise to 1000 ml. of ether. The precipitate is allowed to settle and the solvent decanted. To the residue is added 200 ml. of ethanol, followed by 800 ml. of ether. The precipitated solid is recovered by filtration and dried under high vacuum to obtain the title calcium salt.

EXAMPLE 44

6-(D-2-Amino-2-phenylacetamido)-2,2-dimethyl-3-(O,O-dimethylphosphono)penam Hydrochloride To a solution of 399 mg. (0.001 mole) of 6-(D-2-amino-2-phenylacetamido)-2,2-dimethyl-3-(O,O-dimethylphosphono)penam in 10 ml. of ethanol is added 1.0 ml. of 1.0N ethanolic hydrogen chloride. The resulting solution is cooled in ice whereupon the crystalline title hydrochloride salt precipitates and is collected by filtration and dried in vacuo.

EXAMPLE 45

6-(2-carboxy-2-phenylacetamido)-2,2-dimethyl-3-(O,O-dimethylphosphono)penam Potassium Salt To a stirred solution of 1284 mg. of 6-(2-carboxy-2-phenylacetamido)-2,2-dimethyl-3-(O,O-dimethylphosphono)penam in 75 ml. of methanol, cooled to −30° C. is added dropwise 3.0 ml. of 1.0N potassium hydroxide solution in methanol. The resulting mixture is worked up as described in Example 33 to afford the title potassium salt.

When the above procedure is repeated, but using an equimolar amount of sodium hydroxide in place of the potassium hydroxide used therein, the corresponding sodium salt is obtained.

What is claimed is:

1. A compound of the formula (II)

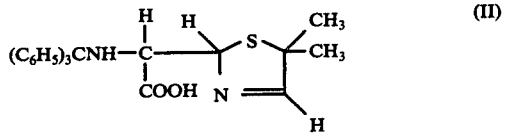

and the sodium and potassium salts thereof.

* * * * *